United States Patent
Wang et al.

(10) Patent No.: US 10,807,979 B2
(45) Date of Patent: Oct. 20, 2020

(54) 4,5-DISUBSTITUTED-1H-PYRROLO(2,3-F) QUINOLIN-2,7,9-TRICARBOXYLATE COMPOUND AND USE THEREOF

(71) Applicant: SHANDONG CAMASY BIOTECHNOLOGY CO., LTD., Jinan, Shandong (CN)

(72) Inventors: Jinglin Wang, Jinan (CN); Song Qin, Jinan (CN); Zhenqiang Mu, Jinan (CN); Yang Li, Jinan (CN)

(73) Assignee: SHANGDONG CAMASY BIOTECHNOLOGY CO., LTD., Jinan (CN)

( * ) Notice: Subject to any disclaimer, the term of this patent is extended or adjusted under 35 U.S.C. 154(b) by 0 days.

(21) Appl. No.: 16/466,198

(22) PCT Filed: May 19, 2017

(86) PCT No.: PCT/CN2017/085108
§ 371 (c)(1),
(2) Date: Jun. 3, 2019

(87) PCT Pub. No.: WO2018/205299
PCT Pub. Date: Nov. 15, 2018

(65) Prior Publication Data
US 2020/0071319 A1    Mar. 5, 2020

(30) Foreign Application Priority Data

May 11, 2017  (CN) .......................... 2017 1 0331083

(51) Int. Cl.
| | | |
|---|---|---|
| *C07D 471/04* | (2006.01) | |
| *C07C 231/10* | (2006.01) | |
| *C07C 231/12* | (2006.01) | |

(52) U.S. Cl.
CPC .......... *C07D 471/04* (2013.01); *C07C 231/10* (2013.01); *C07C 231/12* (2013.01)

(58) Field of Classification Search
CPC .. C07D 471/04; C07D 231/12; C07D 231/10; C07D 231/02; C07D 209/42; C07C 233/25

(Continued)

(56) References Cited

U.S. PATENT DOCUMENTS 4,898,870 A    2/1990   Narutomi et al.

FOREIGN PATENT DOCUMENTS

| CN | 101193888 A | 6/2008 |
| CN | 104557921 A | 4/2015 |

(Continued)

OTHER PUBLICATIONS

Jan. 23, 2018 International Search Report issued in International Patent Application PCT/CN2017/085108.

(Continued)

*Primary Examiner* — Taylor V Oh
(74) *Attorney, Agent, or Firm* — Oliff PLC

(57) ABSTRACT

A 4,5-disubstituted-1H-pyrrolo(2,3-f)quinolin-2,7,9-tricarboxylate compound, or an analog, or derivative thereof, having a structure of Formula I:

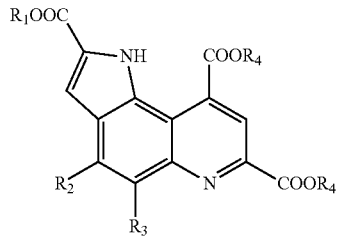

Formula I $R_1$ and $R_4$ are each independently an atom or group selected from hydrogen, a linear or branched C1-8 alkyl group, a deuterated linear or branched C1-8 alkyl group, an aralkyl group, or a substituted aryl group; $R_2$ is independently an atom or group selected from halogens, a linear or branched C1-8 alkoxy group, or a deuterated linear or branched C1-8

(Continued)

alkoxy group; and $R_3$ is independently an atom or group selected from a linear or branched C1-8 alkoxy group, or a deuterated linear or branched C1-8 alkoxy group. The compound is useful as a reaction intermediate for the synthesis of PQQ. A process in which CAN is used as an oxidant in the synthesis of PQQ in existing patents and literatures is replaced. This makes the process cheaper and more efficient.

17 Claims, 21 Drawing Sheets

(58) Field of Classification Search
USPC .......................................................... 546/84
See application file for complete search history.

(56) References Cited

FOREIGN PATENT DOCUMENTS

| CN | 105473544 A | 4/2016 |
|---|---|---|
| WO | 2006/102642 A1 | 9/2006 |
| WO | 2014/195896 A1 | 12/2014 |

OTHER PUBLICATIONS

Jan. 23, 2018 Written Opinion issued in International Patent Application PCT/CN2017/085108.

Gainor et al; "Synthesis of the Bacterial Coenzyme Methoxatin"; J. Org. Chem.; Dec. 31, 1982; vol. 47 pp. 2833-2837.
Gibson et al; "The Nitration of 2-Acetylamino-3:4-dimethoxy-benzoic Acid and 3-Acetylaminoveratrole."; Journal of the Chemical Society; vol. 111; Jan. 1, 1917; pp. 69-85.
E.J. Corey et al; "Total Synthesis of the Quinonoid Alcohol Dehydrogenase Coenzyme (1) of Methylotrophic Bacteria"; J. Am. Chem. Soc.; 1981; vol. 103; pp. 5599-5600.
Pierre Martin; "Ein eingacher Zugang zu PQQ"; Helvetica Chimica Acta; vol. 76; 1993; pp. 988-992.
Robert A. van der Meer, et al; "Determination of PQQ in quinoproteins with covalently bound cofactor and in PQQ-derivatives"; Aug. 1989; vol. 254; No. 1-2; pp. 99-105.
Fang Dong, et al; "Advance in Quinoprotein Research"; Letter in Biotechnology; Jan. 2007; vol. 18; No. 1; pp. 132-136.
Mercedes A. Paz, et al; "The Catalysis of Redox Cycling by Pyrroloquinoline Quinone (PQQ), PQQ Derivatives, and Isomoers and the Specificity of Inhibitors"; 1996; Analytical Biochemistry 238; Article No. 0267; pp. 145-149.
Von Pierre Martin, et al; "109. Zur Herstellung von PQQ in kg-Mengen"; Helvetica Chimica Acta; 1993; vo. 76; pp. 1667-1673.
David B. Reitz, et al; "Total Synthesis of Methoxatin, the Coenzyme of Methanol Dehydrogenase and Glucose Dehydrogenase"; J. Org. Chem.; 1981; vol. 46; pp. 4317-4319.
Oct. 10, 2017 Office Action Issued in Chinese Patent Application No. 201710331083.6.
Jan. 9, 2018 Office Action Issued in Chinese Patent Application No. 201710331083.6.

4,5-DISUBSTITUTED-1H-PYRROLO(2,3-F) QUINOLIN-2,7,9-TRICARBOXYLATE COMPOUND AND USE THEREOF

BACKGROUND

Technical Field

The present invention relates to the technical field of preparation of organic compounds, and particularly to a 4,5-disubstituted-1H-pyrrolo(2,3-f)quinolin-2,7,9-tricarboxylate compound, and a preparation method and use thereof.

Related Art

Pyrroloquinoline quinone (PQQ) is a natural product, also known as methoxatin. Among many uses, the primary use of PQQ is to protect the mitochondria against oxidative stress, and provide neuroprotection and myocardial protection. Common food sources for PQQ include parsley, green pepper, green tea, papaya, kiwi and milk. However, the concentration of PQQ in food sources just varies from nanograms (ng) to micrograms (μg) per kilogram. Therefore, it is difficult to guarantee sufficient PQQ acquisition through dietary supplementation, and it is necessary to develop a chemical method to synthesize PQQ in large scales.

The first total synthesis of PQQ was conducted by Corey et al. [J. Am. Chem. Soc. 103 (1981), 5599-5600]. As reported by Corey, PQQ can be prepared from commercial raw materials by a 10-step chemical process. However, only 50 mg of PQQ can be obtained following the reported process.

Subsequently, the Corey's route to PQQ was modified by Martin et al. [HelvChemActa76 (1993)], and the total synthesis steps are reduced to 9 steps. However, the overall process route is very similar, and the production scale is not significantly improved.

In 2006, the novel synthesis of PQQ was reported in WO 2006/102642 A1 issued to Kempf et al. This application mainly discloses the large-scale synthesis of PQQ by combining the Corey's and Martin's routes. This application further claims the purification of the end compound with sulfuric acid.

In 2014, India Anser Biotech Pte. Ltd. publicized the patent WO2014/195896 concerning PQQ synthesis. The novelty of this application from others lies in that PQQ can be synthesized at a large scale with methyl halobenzene as a raw material. However, at the vital step to grantee the full chemical synthesis of PQQ, the methoxy-pyrroloquinoline intermediate needs to be mildly oxidized into a pyrroloquinoline quinone intermediate by ammonium cerium nitrate (CAN). Although the process exhibits a high selectivity to product, the consumption of ammonium cerium nitrate is extremely large (more than 8 times the weight of the raw material), and the optimum yield of this step is only approximately 60% due to the difficulty in the separation and purification. In addition, the high price of CAN makes the overall synthesis cost of PQQ high; and the cerium salt can only be treated as waste, and therefore the sewage discharge load is high. In addition, due to the low efficiency of the process, it is difficult to achieve efficient industrial production of PQQ.

SUMMARY

In view of the prior art, a first object of the present invention is to provide an improved method for synthesizing PQQ, which avoids the use of ammonium cerium nitrate and becomes a key route for inexpensive and large-scale synthesis of PQQ.

A second object of the present invention is to provide a reaction intermediate for synthesizing PQQ and a method for preparing the reaction intermediate.

To achieve the above object, the present invention adopts the following technical solutions.

A first aspect of the present invention provides a compound of Formula I, or an analogue, isomer or derivative thereof:

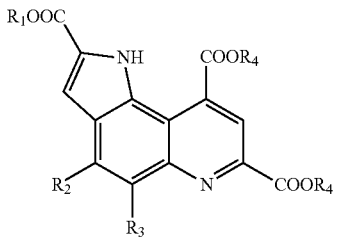

Formula I where $R_1$ and $R_4$ are each independently an atom or group selected from hydrogen, a linear or branched C1-8 alkyl group, a deuterated linear or branched C1-8 alkyl group, an aralkyl group, or a substituted aryl group;

$R_2$ is independently an atom or group selected from halogens, a linear or branched C1-8 alkoxy group, or a deuterated linear or branched C1-8 alkoxy group; and $R_3$ is independently an atom or group selected from a linear or branched C1-8 alkoxy group, or a deuterated linear or branched C1-8 alkoxy group.

Preferably, $R_1$ and $R_4$ are each independently selected from hydrogen, methyl or ethyl; $R_2$ is selected from halogens or a C1-4 alkoxy group; and $R_3$ is selected from a C1-4 alkoxy group.

Preferably, the compound of Formula I is selected from:

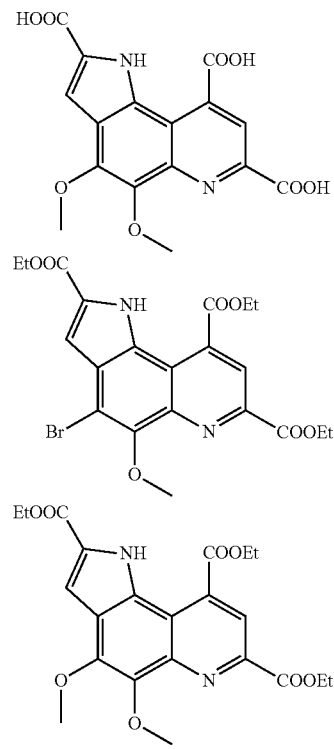

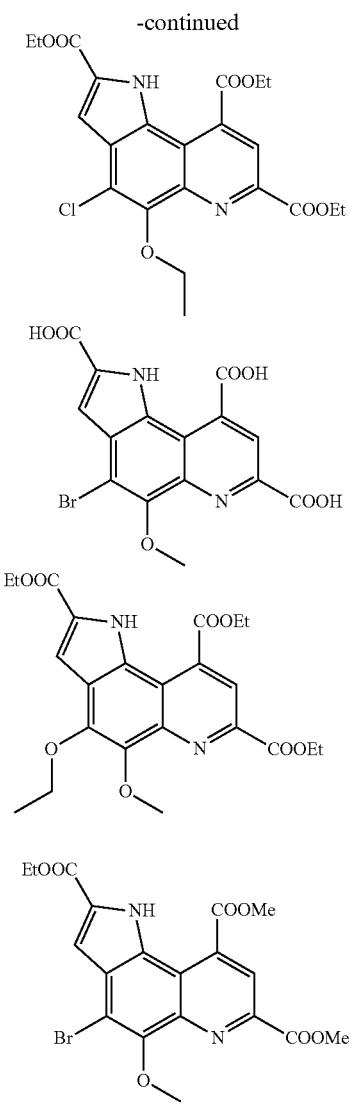

A second aspect of the present invention provides an intermediate for preparing the compound of Formula I, which has a structure of Formula III:

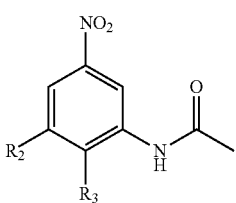

Formula III where $R_2$ is independently an atom or group selected from halogens, a linear or branched C1-8 alkoxy group, or a deuterated linear or branched C1-8 alkoxy group; and $R_3$ is independently an atom or group selected from a linear or branched C1-8 alkoxy group, or a deuterated linear or branched C1-8 alkoxy group.

The present invention also provides a method for synthesizing the compound of Formula III, in which NBS or NCS is used as a halogen source, concentrated sulfuric acid or methanesulfonic acid is used as a solvent, a substrate is added, and then reacted, to obtain the compound of Formula III.

In the method, the substrate has a structural formula of:

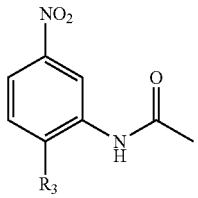

where $R_3$ is independently an atom or group selected from a linear or branched C1-8 alkoxy group, or a deuterated linear or branched C1-8 alkoxy group.

In the method, the molar ratio of the substrate, halogen source and solvent is 1:(0.95-1.5):(3-12).

In the method, the halogen source is preferably NBS.

In the method, the reaction temperature is 20-60° C.

The compound of Formula III can be used as an intermediate for preparing the compound of Formula I, and is further used for preparing PQQ.

A fourth aspect of the present invention provides an intermediate for preparing the compound of Formula I, which has a structure of Formula IV:

Formula IV where $R_2$ is independently an atom or group selected from halogens, a linear or branched C1-8 alkoxy group, or a deuterated linear or branched C1-8 alkoxy group; and $R_3$ is independently an atom or group selected from a linear or branched C1-8 alkoxy group, including a deuterated linear or branched C1-8 alkoxy group.

The compound of Formula IV is prepared by a nitro reducing reaction of the compound of Formula III.

The compound of Formula IV can be used as an intermediate for preparing the compound of Formula I, and is further used for preparing PQQ.

A fifth aspect of the present invention provides an intermediate for preparing the compound of Formula I, which has a structure of Formula V:

Formula V where $R_1$ is independently an atom or group selected from hydrogen, a linear or branched C1-8 alkyl group, a deuterated linear or branched C1-8 alkyl group, an aralkyl group, or a substituted aryl group;

R$_2$ is independently an atom or group selected from halogens, a linear or branched C1-8 alkoxy group, or a deuterated linear or branched C1-8 alkoxy group; and R$_3$ is independently an atom or group selected from a linear or branched C1-8 alkoxy group, including a deuterated linear or branched C1-8 alkoxy group.

The compound of Formula V is obtained by Fischer synthesis by diazotizing the compound of Formula IV, and then reacting with 2-methyl acetoacetate.

The compound of Formula V can be used as an intermediate for preparing the compound of Formula I, and is further used for preparing PQQ.

A sixth aspect of the present invention provides an intermediate for preparing the compound of Formula I, which has a structure of Formula II:

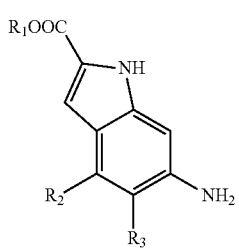

Formula II where R$_1$ is independently an atom or group selected from hydrogen, a linear or branched C1-8 alkyl group, a deuterated linear or branched C1-8 alkyl group, an aralkyl group or a substituted aryl group;

R$_2$ is independently an atom or group selected from halogens, a linear or branched C1-8 alkoxy group, or a deuterated linear or branched C1-8 alkoxy group; and R$_3$ is independently an atom or group selected from a linear or branched C1-8 alkoxy group, or a deuterated linear or branched C1-8 alkoxy group.

The compound of Formula II is prepared by deacylation of the compound of Formula V.

The compound of Formula II can be used as an intermediate for preparing the compound of Formula I, and is further used for preparing PQQ.

A seventh aspect of the present invention provides a method for synthesizing the compound of Formula I.

The synthesis method provided in the present invention comprises a step of: obtaining the compound of Formula II by nitro reduction, Fischer indole synthesis and deacylation using the compound of Formula III as a raw material; and a step of obtaining the compound of Formula I by subjecting the compound of Formula II to Skraup quinoline synthesis.

Preferably, the method for obtaining the compound of Formula I by subjecting the compound of Formula II to Skraup quinoline synthesis comprises specifically dissolving the compound of Formula II in an organic solvent, adding dimethyl 2-oxopentendioate or diethyl 2-oxopentendioate, reacting with stirring at room temperature, evaporating off the solvent, and recrystallizing the residue.

To make the synthesis of the compound of Formula I clearer and more complete, the present invention provides a route for synthesizing the compound of Formula I, which is specifically as follows:

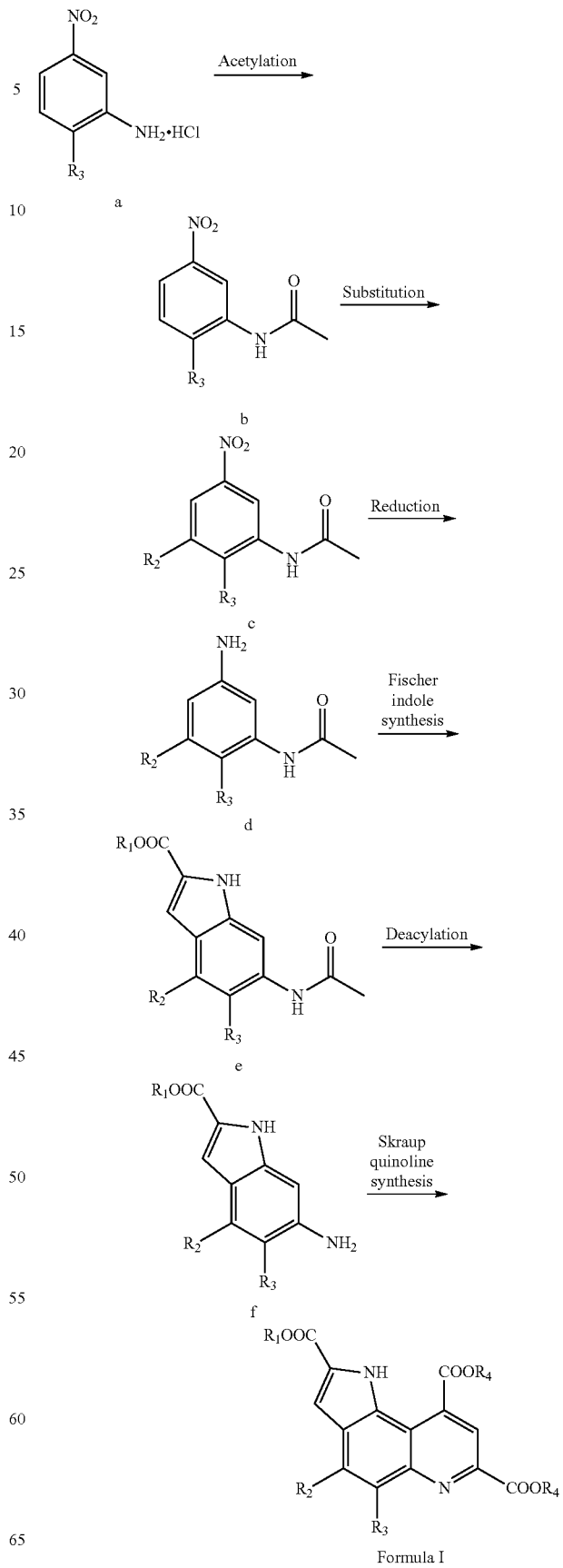

Formula I

It can be seen from the above synthesis route that the whole process for synthesizing the compound of Formula I of the present invention includes at least the following reaction steps:

(1) acetylating Compound a that is a raw material to obtain Compound b;

(2) halogenating/substituting Compound b to obtain Compound c;

(3) subjecting Compound c to nitro reduction to obtain Compound d;

(4) obtaining Compound e by Fischer synthesis by diazotizing Compound d, and then reacting with 2-methyl acetoacetate;

(5) deacylating Compound e to obtain Compound f; and (6) obtaining the compound of Formula I by Skraup reaction by condensing Compound f with 2-oxopentendioate.

Use of the compound of Formula I in the synthesis of PQQ is also within the scope of the present invention.

An eighth aspect of the present invention provides a method for synthesizing PQQ.

The method for synthesizing PQQ provided in the invention comprises the following steps:

(1) reacting the compound of Formula I with a base or a protonic acid to obtain a compound of formula VI;

(2) reacting the compound of Formula VI with a protonic acid to obtain reduced PQQ, that is, PQP; and (3) oxidizing PQP with an oxidizing agent to obtain PQQ.

In Step (1), the method for reacting the compound of Formula I with a base or a protonic acid to obtain the compound of Formula VI comprises: adding the compound of Formula I to an alkali liquor or a protonic acid, reacting under reflux by heating, cooling to room temperature after the reaction is completed, filtering under suction, adjusting the pH of the filtrate to less than 2, washing, and drying.

Preferably, in Step (1), the base is NaOH or KOH; and the protonic acid is hydroiodic acid, hydrochloric acid or hydrobromic acid.

In Step (2), the method for reacting the compound of Formula VI with a protonic acid to obtain PQP comprises: adding the compound of Formula VI to acetic acid, adding a protonic acid solution dropwise, mixing uniformly, reacting under reflux, adding the reaction solution to ice water after the reaction is completed to precipitate a solid out, filtering under suction, washing, drying, and recrystallizing in ethanol.

Preferably, in Step (2), the protonic acid is hydroiodic acid, hydrochloric acid or hydrobromic acid, and further preferably hydroiodic acid.

Preferably, in Step (3), the oxidizing agent is hydrogen peroxide, concentrated sulfuric acid, concentrated nitric acid or ozone.

The route for synthesizing PQQ of the present invention is:

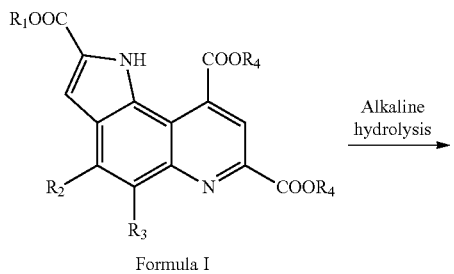

Formula I

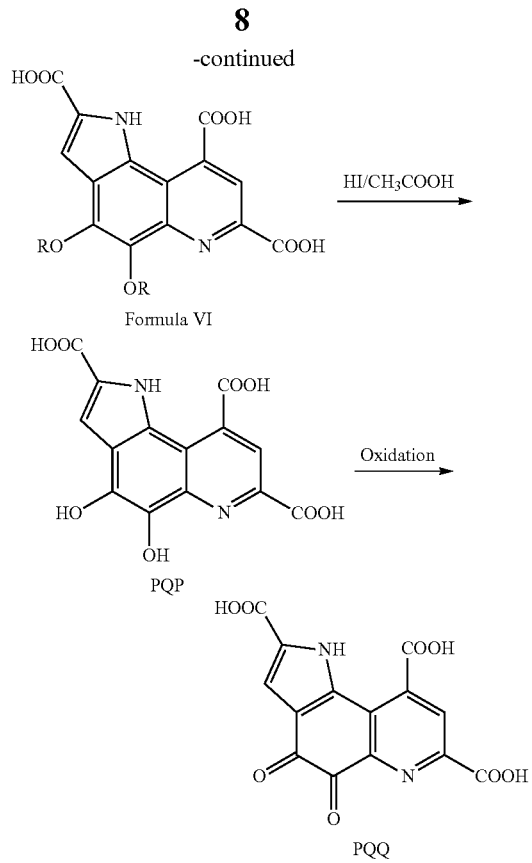

where in Formula VI, R=Me or Et.

The above technical solution has the following beneficial effects:

(1) In the present invention, an inexpensive and easy-get raw material is used, and the full synthesis of PQQ is realized by synthesizing the compound of Formula I. In the present invention, an $R_2$ group that is a readily oxidizable and stable substituent is introduced to the compound of Formula I, thus providing a more convenient reaction condition for the preparation of PQQ in the next step; and no expensive oxidant is needed, whereby a process in which CAN is used as an oxidant in the synthesis of PQQ in existing patents and literatures is replaced. This makes the whole process cheaper and more efficient, reduces the waste discharge throughout the process, and optimizes the economic and environmental benefits of the entire process.

(2) By using the method for synthesizing PQQ according to the present invention, the PQQ synthesis at a scale of "kg" or more can be realized, and the yield of the product is high, which are advantageous for industrial production.

DETAILED DESCRIPTION

Figure 1:
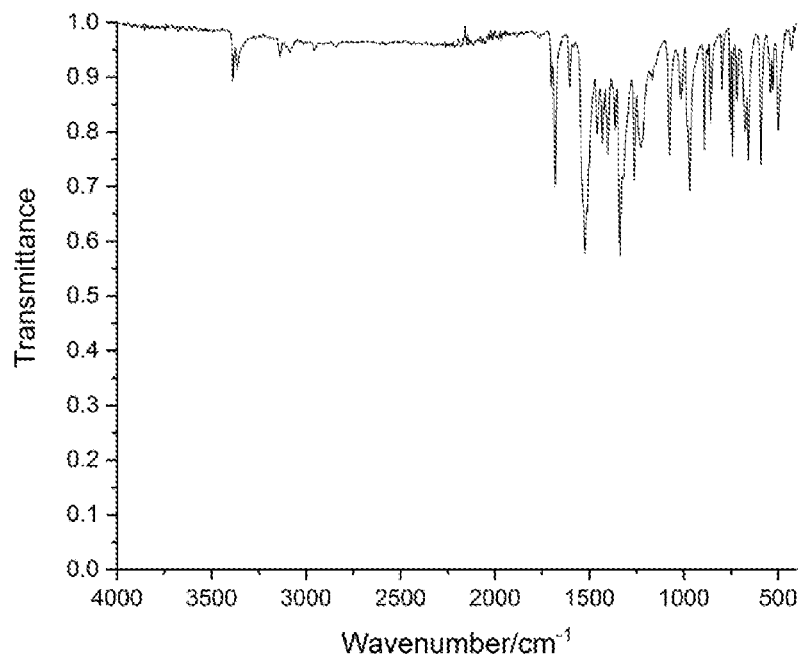
FIG. 1 shows an IR spectrum of Compound 3, that is, 2-methoxy-3-bromo-5-nitro-acetylaniline.
Figure 2:
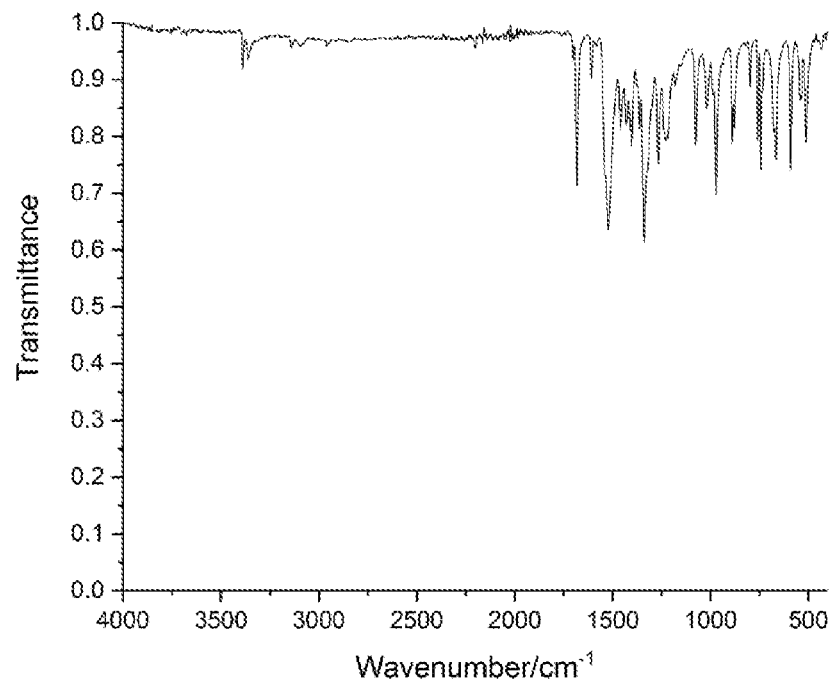
FIG. 2 shows an IR spectrum of 2-methoxy-3-chloro-5-nitro-acetylaniline.
Figure 3:
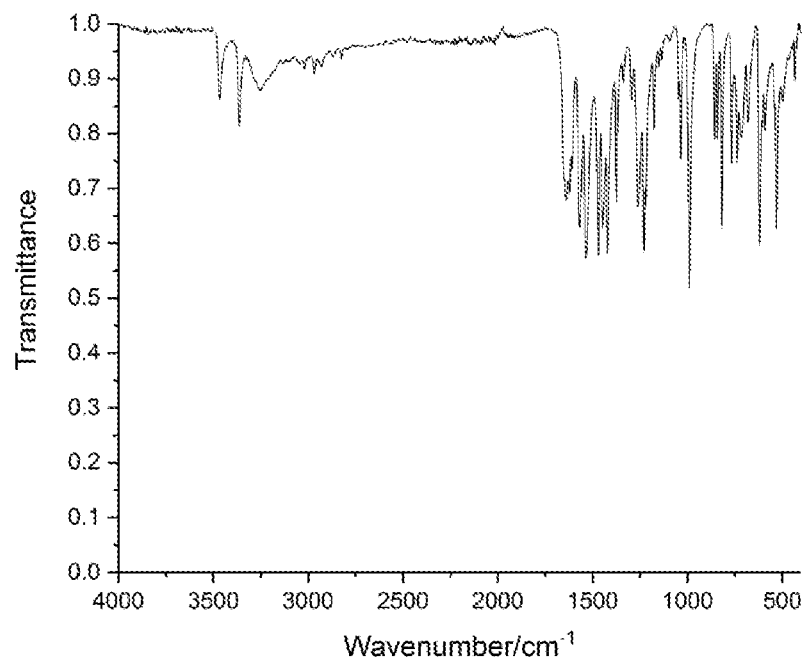
FIG. 3 shows an IR spectrum of Compound 4, that is, 2-methoxy-3-bromo-5-amino-acetylaniline.
Figure 4:
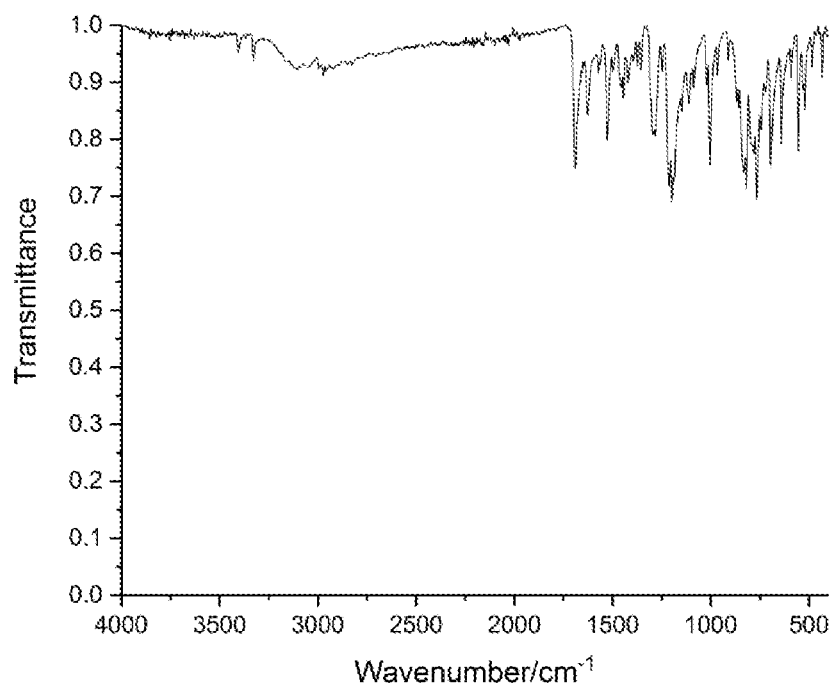
FIG. 4 shows an IR spectrum of Compound 6, that is, ethyl 6-amino-4-bromo-5-methoxy-1H-iodol-2-carboxylate.
Figure 5:
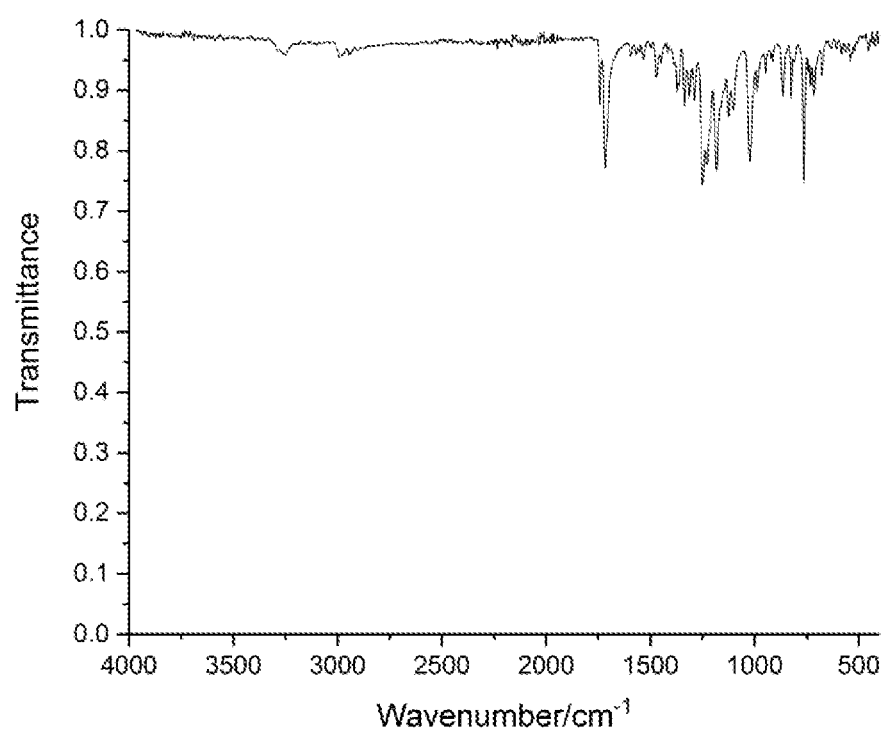
FIG. 5 shows an IR spectrum of Compound 7, that is, triethyl 4-bromo-5-methoxy-1H-pyrrolo(2,3-f)quinolin-2,7,9-tricarboxylate.
Figure 6:
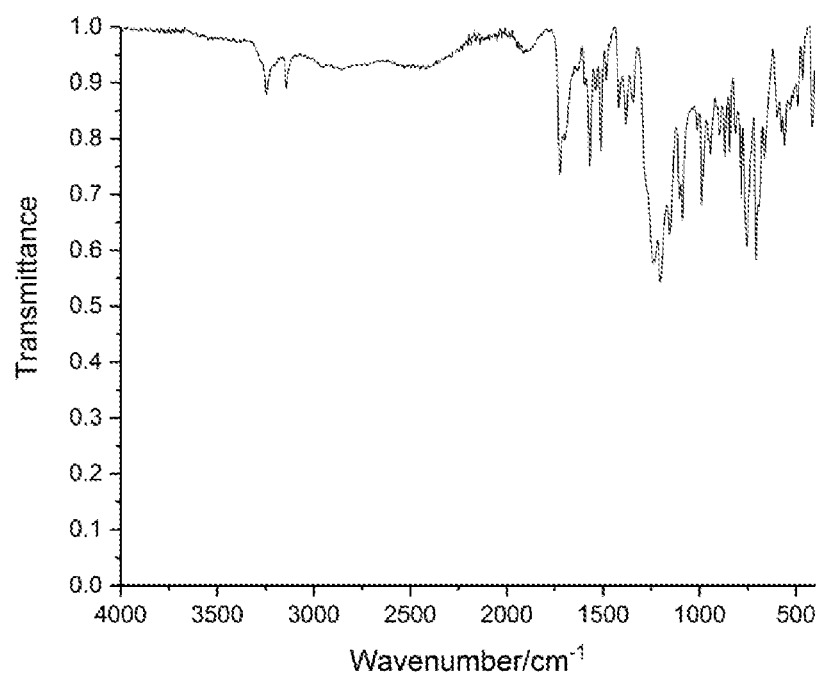
FIG. 6 shows an IR spectrum of Compound 8, that is, 4,5-dimethoxy-1H-pyrrolo(2,3-f)quinolin-2,7,9-tricarboxylic acid.
Figure 7:
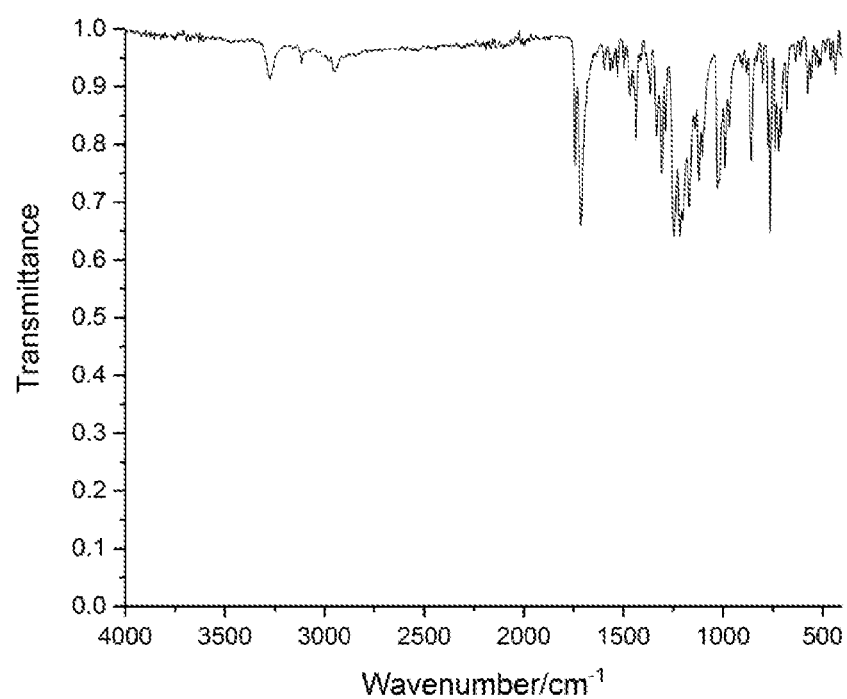
FIG. 7 shows an IR spectrum of Compound 11, that is, 2-ethyl 7,9-dimethyl 4-bromo-5-methoxy-1H-pyrrolo(2,3-f)quinolin-2,7,9-tricarboxylate.
Figure 8:
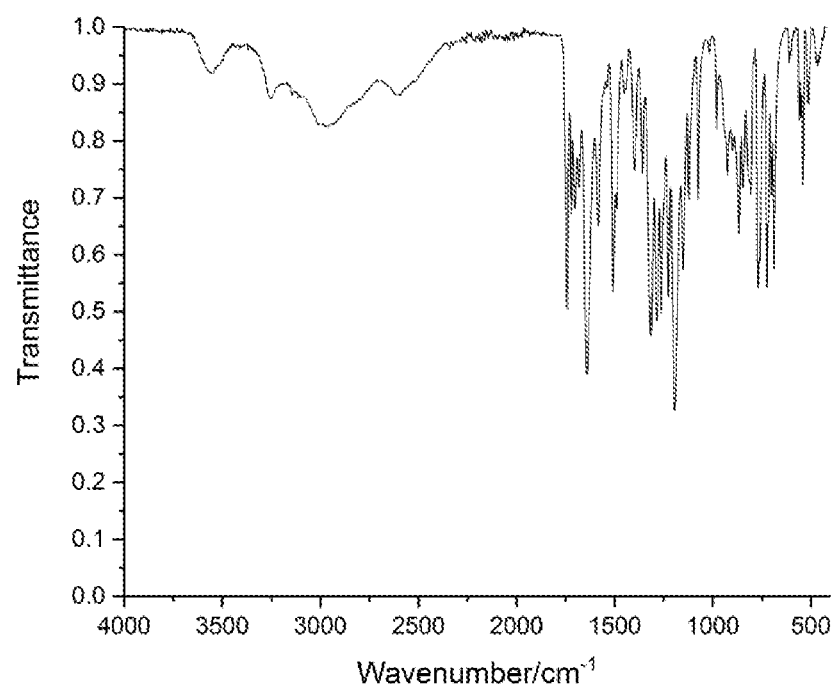
FIG. 8 shows an IR spectrum of PQQ, that is, pyrroloquinoline quinone.
Figure 9:
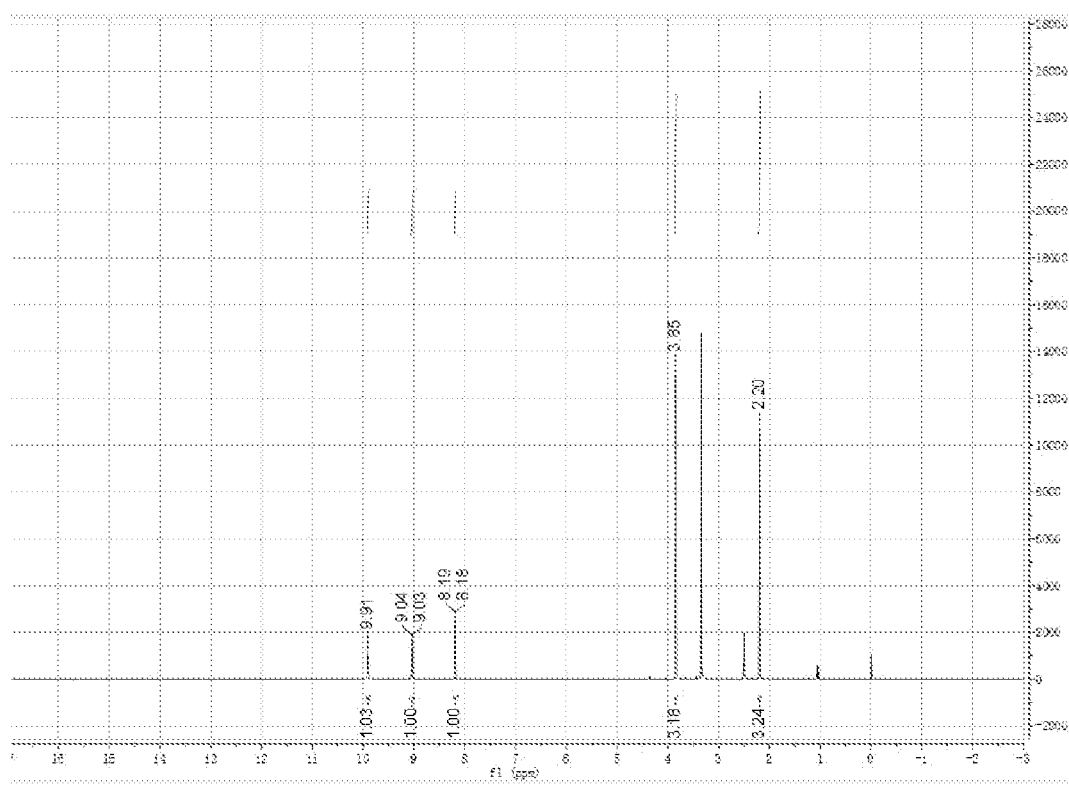
FIG. 9 shows a $^1$H-NMR spectrum of Compound 3, that is, 2-methoxy-3-bromo-5-nitro-acetylaniline.
Figure 10:
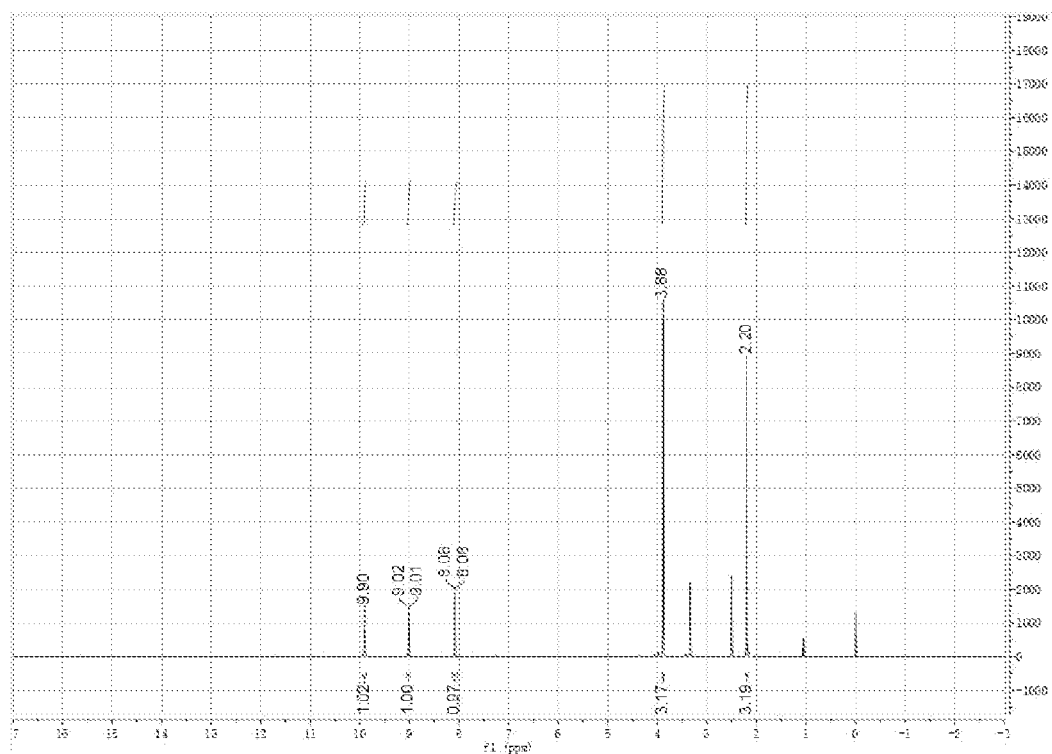
FIG. 10 shows a $^1$H-NMR spectrum of 2-methoxy-3-chloro-5-nitro-acetylaniline.
Figure 11:
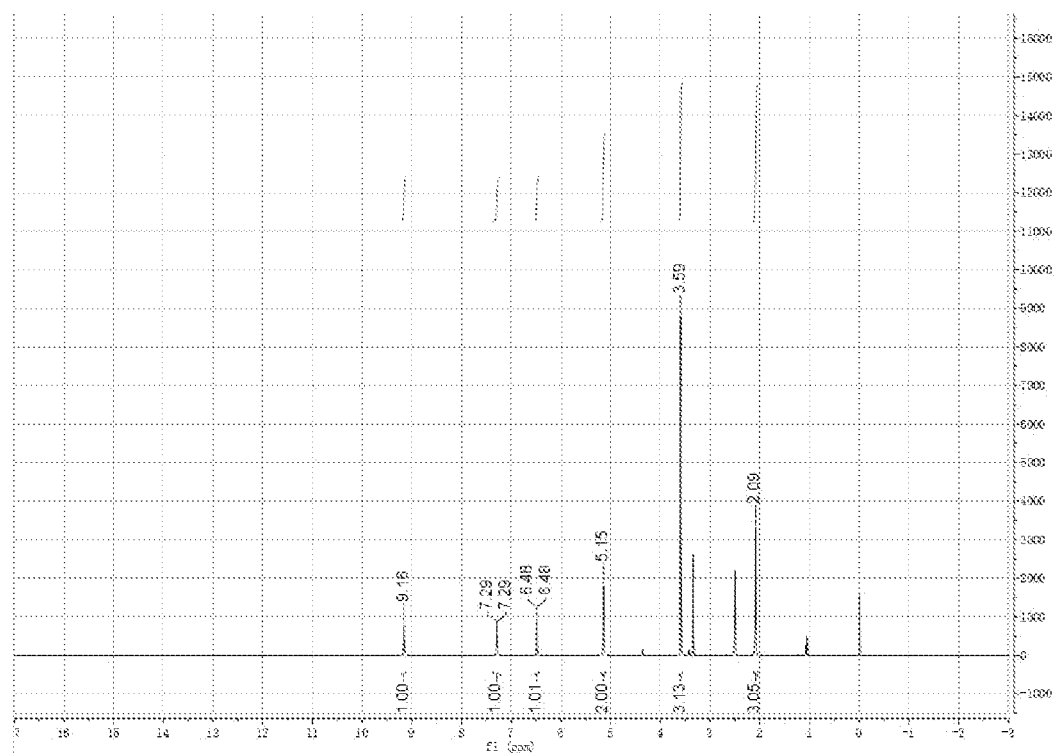
FIG. 11 shows a $^1$H-NMR spectrum of Compound 4, that is, 2-methoxy-3-bromo-5-amino-acetylaniline.
Figure 12:
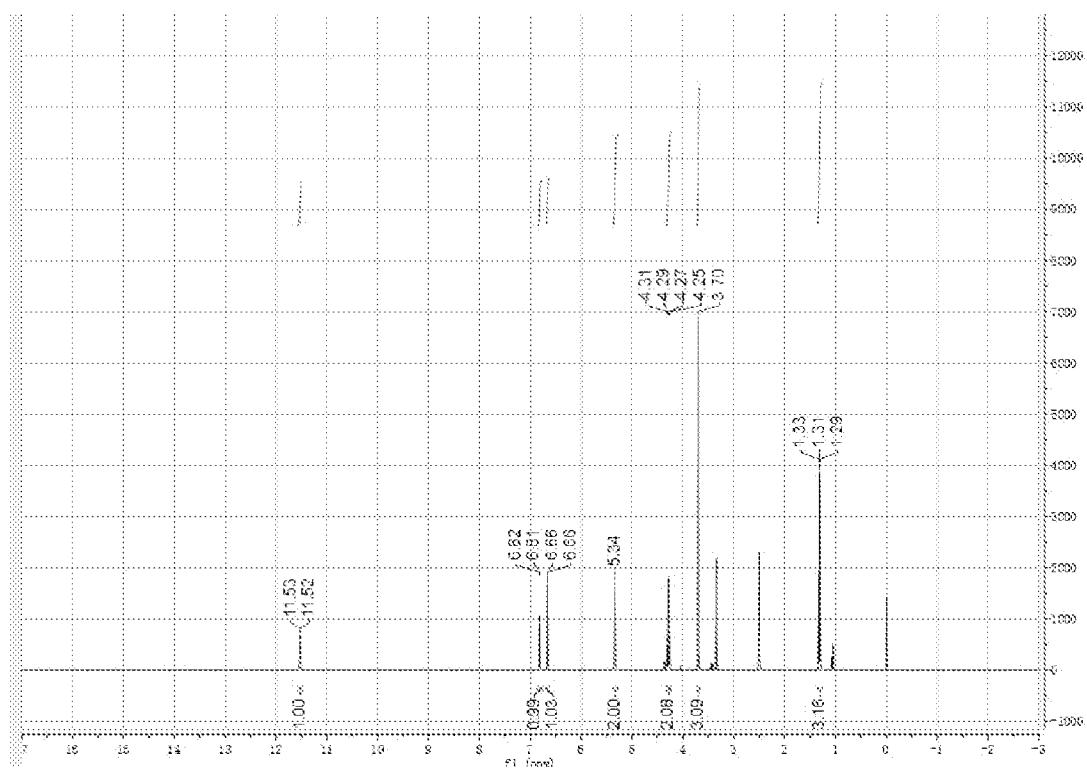
FIG. 12 shows a $^1$H-NMR spectrum of Compound 6, that is, ethyl 6-amino-4-bromo-5-methoxy-1H-indol-2-carboxylate.
Figure 13:
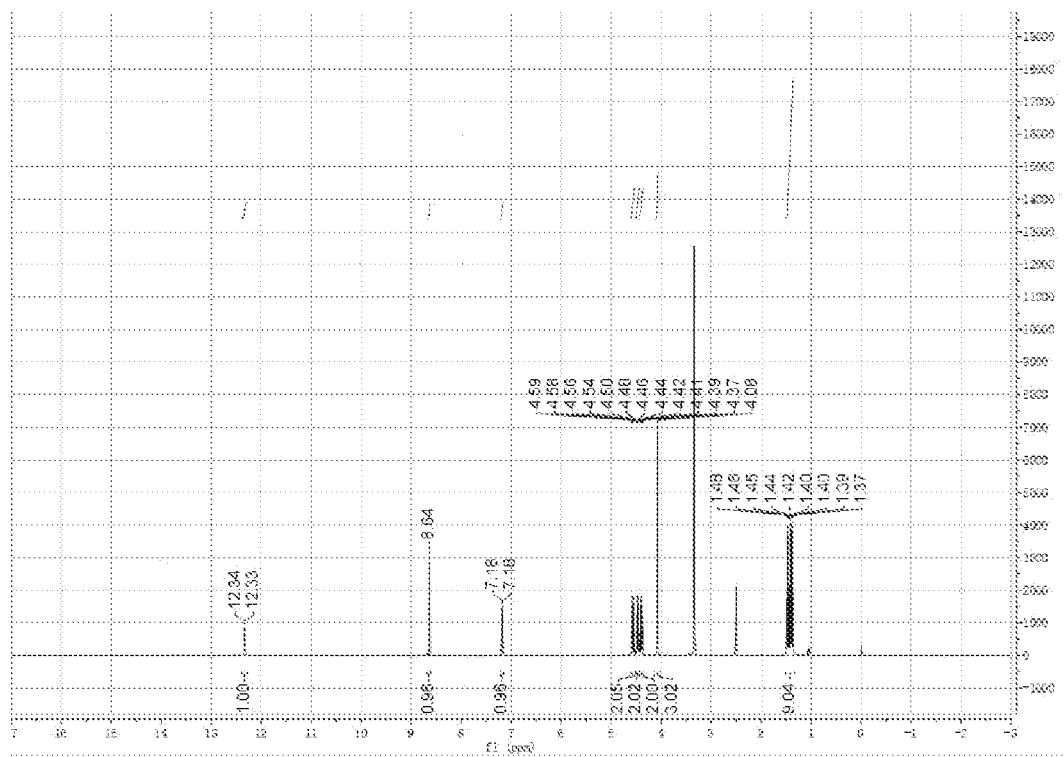
FIG. 13 shows a $^1$H-NMR spectrum of Compound 7, that is, triethyl 4-bromo-5-methoxy-1H-pyrrolo(2,3-f)quinolin-2,7,9-tricarboxylate.
Figure 14:
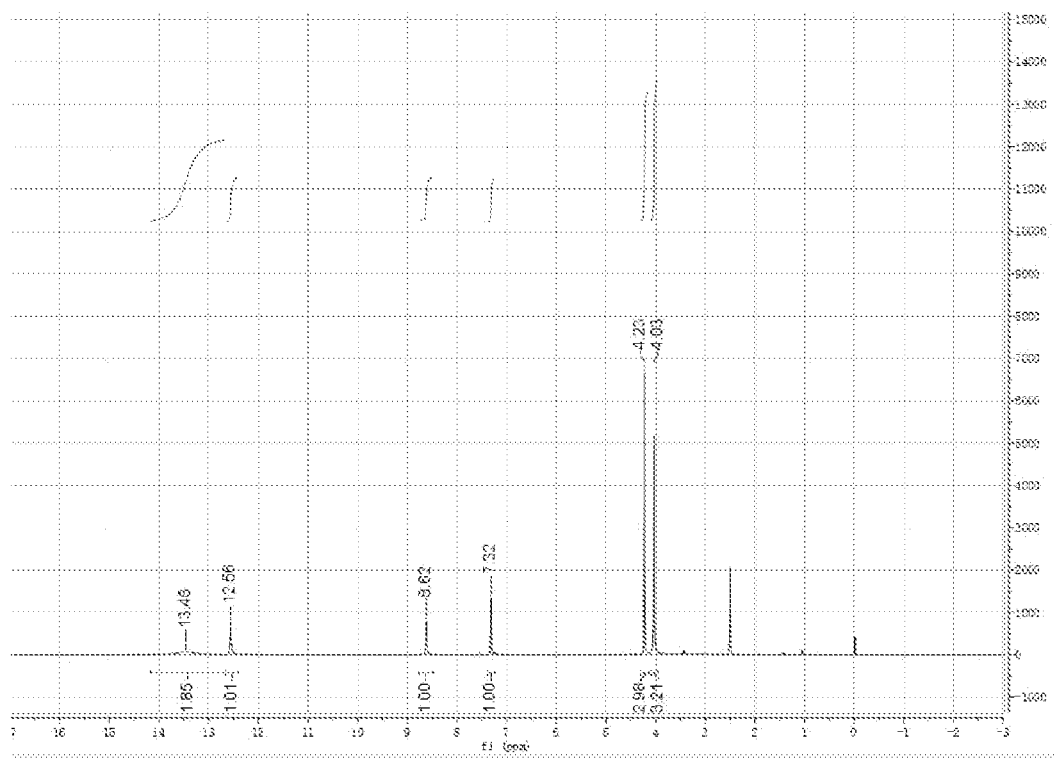
FIG. 14 shows a $^1$H-NMR spectrum of Compound 8, that is, 4,5-dimethoxy-1H-pyrrolo(2,3-f)quinolin-2,7,9-tricarboxylic acid.
Figure 15:
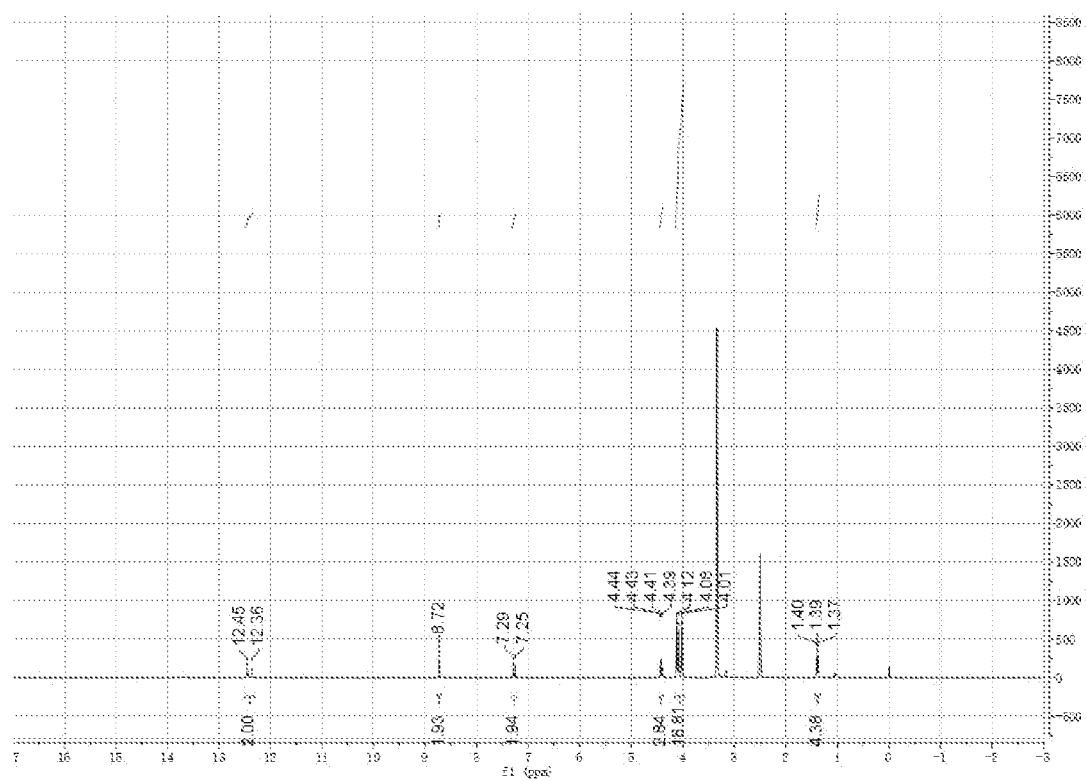
FIG. 15 shows a $^1$H-NMR spectrum of Compound 11, that is, 2-ethyl 7,9-dimethyl 4-bromo-5-methoxy-1H-pyrrolo(2,3-f)quinolin-2,7,9-tricarboxylate.
Figure 16:
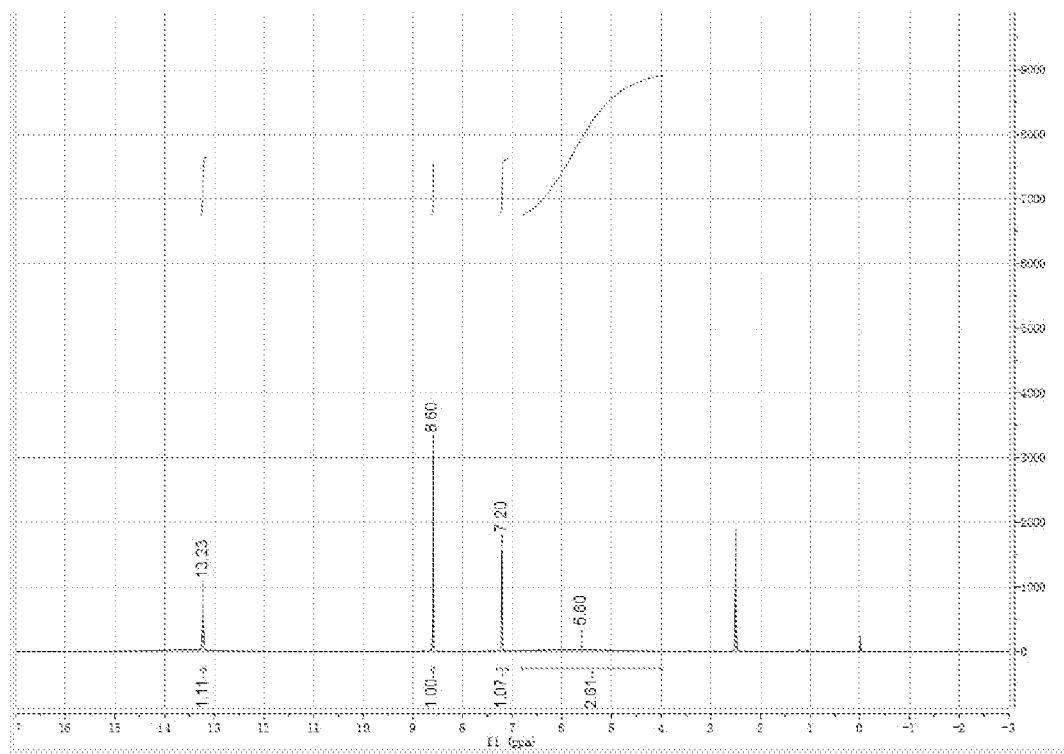
FIG. 16 shows a $^1$H-NMR spectrum of PQQ, that is, pyrroloquinoline quinone.
Figure 17:
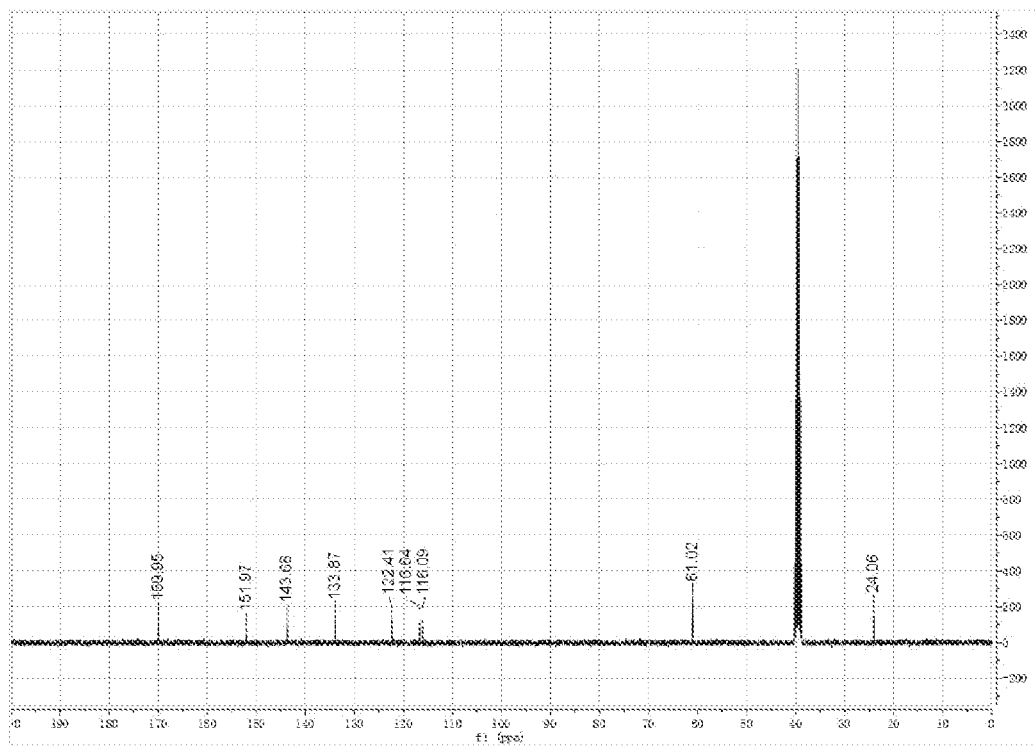
FIG. 17 shows a $^{13}$C-NMR spectrum of Compound 3, that is, 2-methoxy-3-bromo-5-nitro-acetylaniline.
Figure 18:
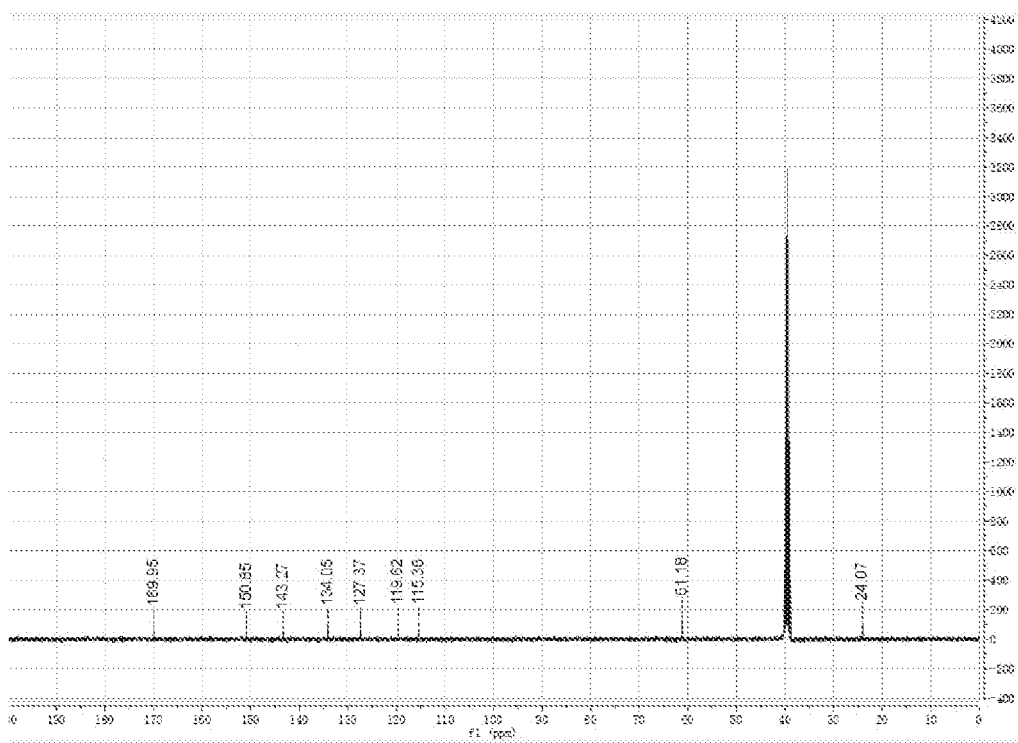
FIG. 18 shows a $^{13}$C-NMR spectrum of 2-methoxy-3-chloro-5-nitro-acetylaniline.
Figure 19:
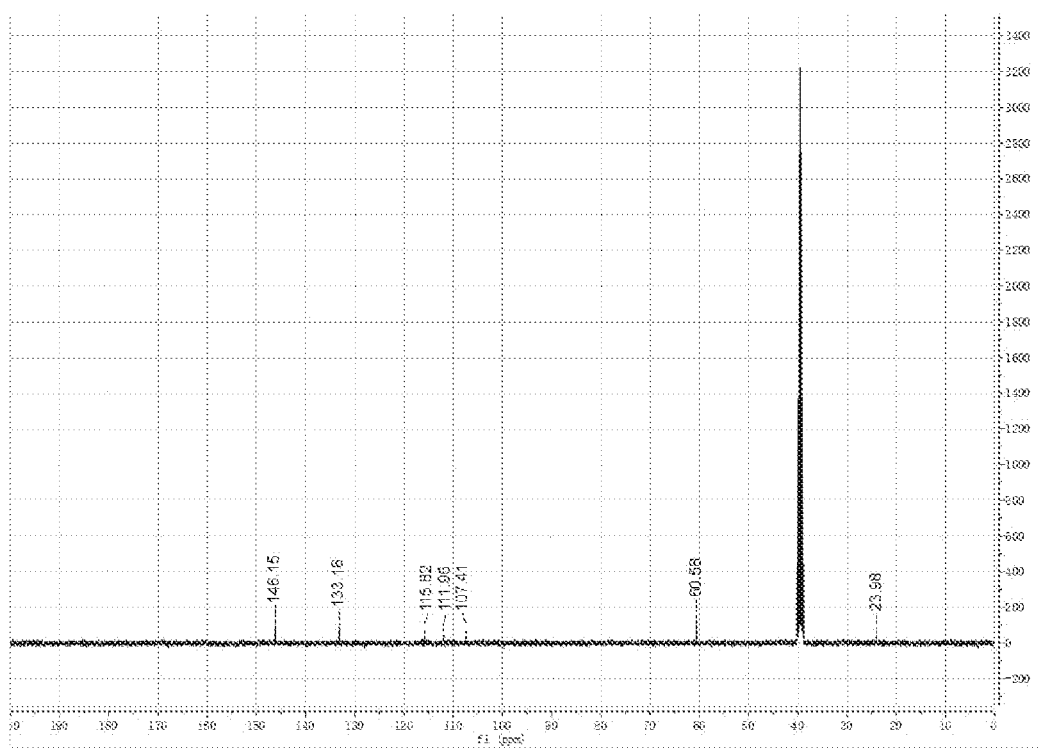
FIG. 19 shows a $^{13}$C-NMR spectrum of Compound 4, that is, 2-methoxy-3-bromo-5-amino-acetylaniline.
Figure 20:
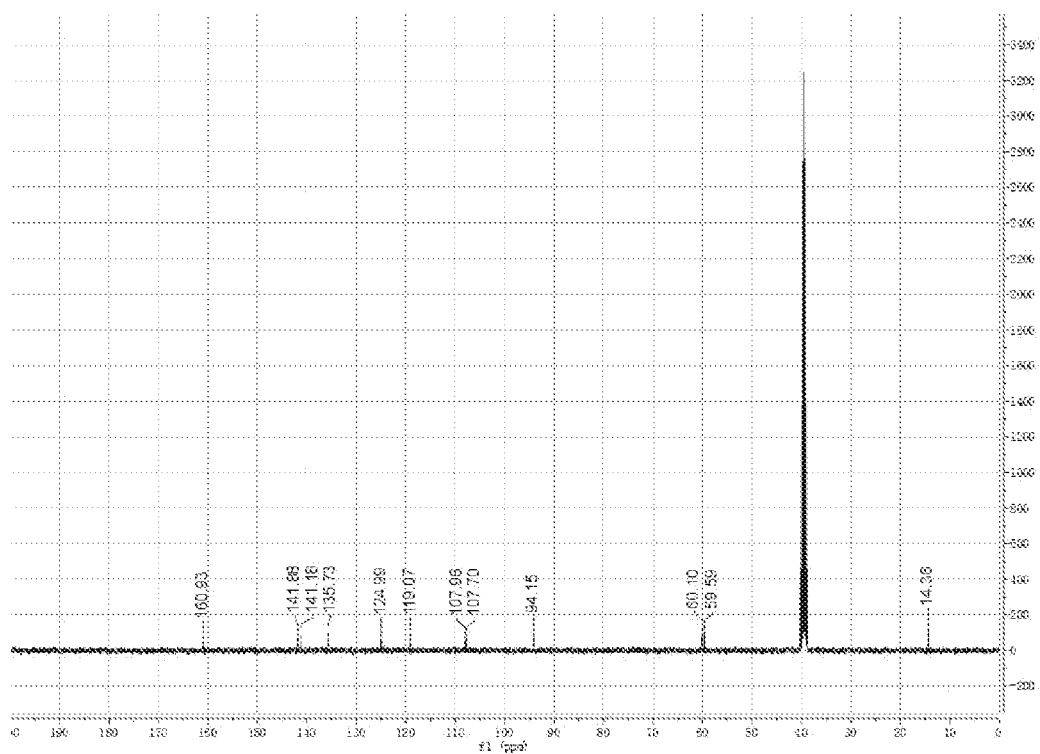
FIG. 20 shows a $^{13}$C-NMR spectrum of Compound 6, that is, ethyl 6-amino-4-bromo-5-methoxy-1H-indol-2-carboxylate.
Figure 21:
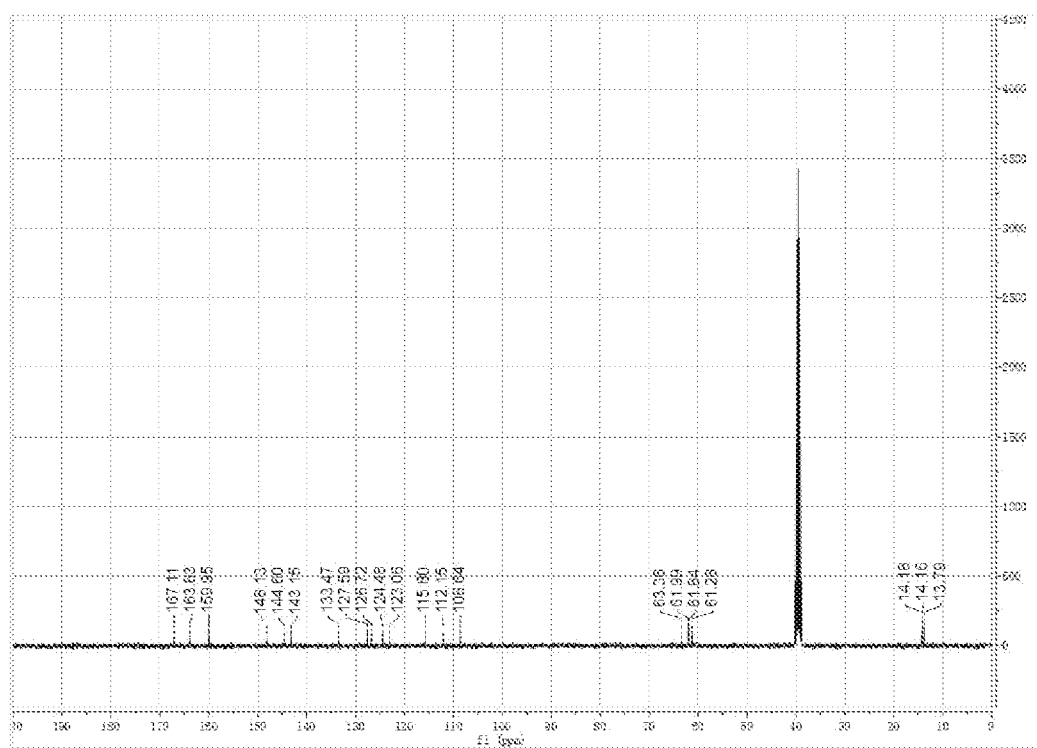
FIG. 21 shows a $^{13}$C-NMR spectrum of Compound 7, that is, triethyl 4-bromo-5-methoxy-1H-pyrrolo(2,3-f)quinolin-2,7,9-tricarboxylate.
Figure 22:
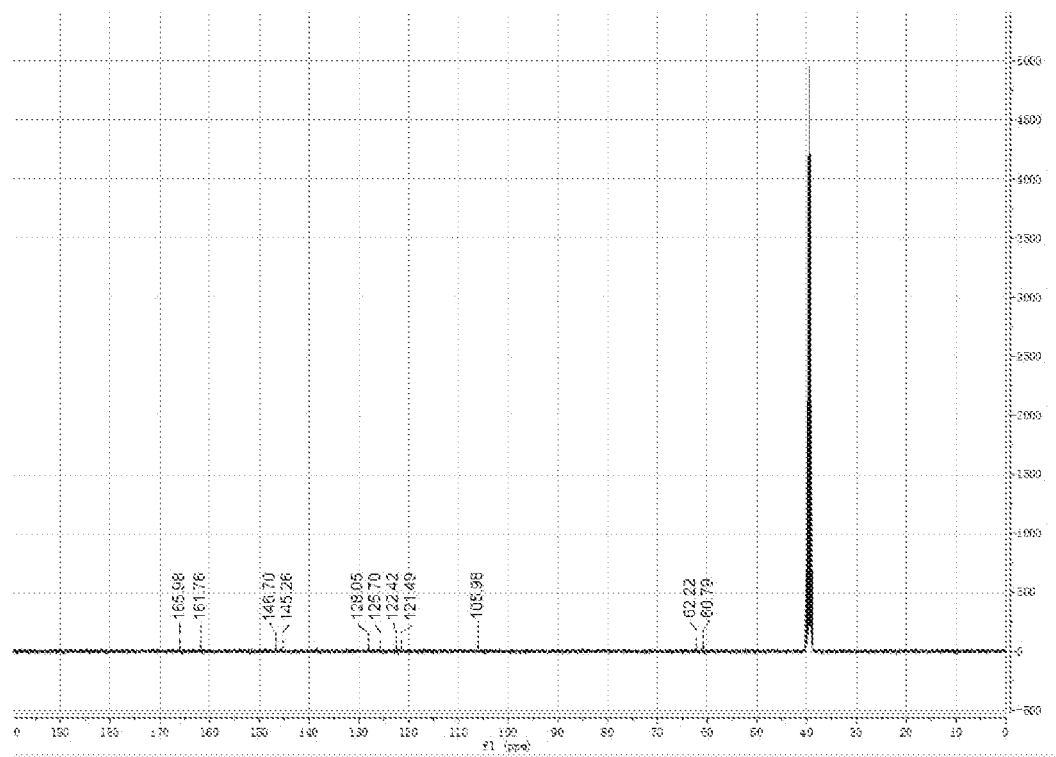
FIG. 22 shows a $^{13}$C-NMR spectrum of Compound 8, that is, 4,5-dimethoxy-1H-pyrrolo(2,3-f)quinolin-2,7,9-tricarboxylic acid.
Figure 23:
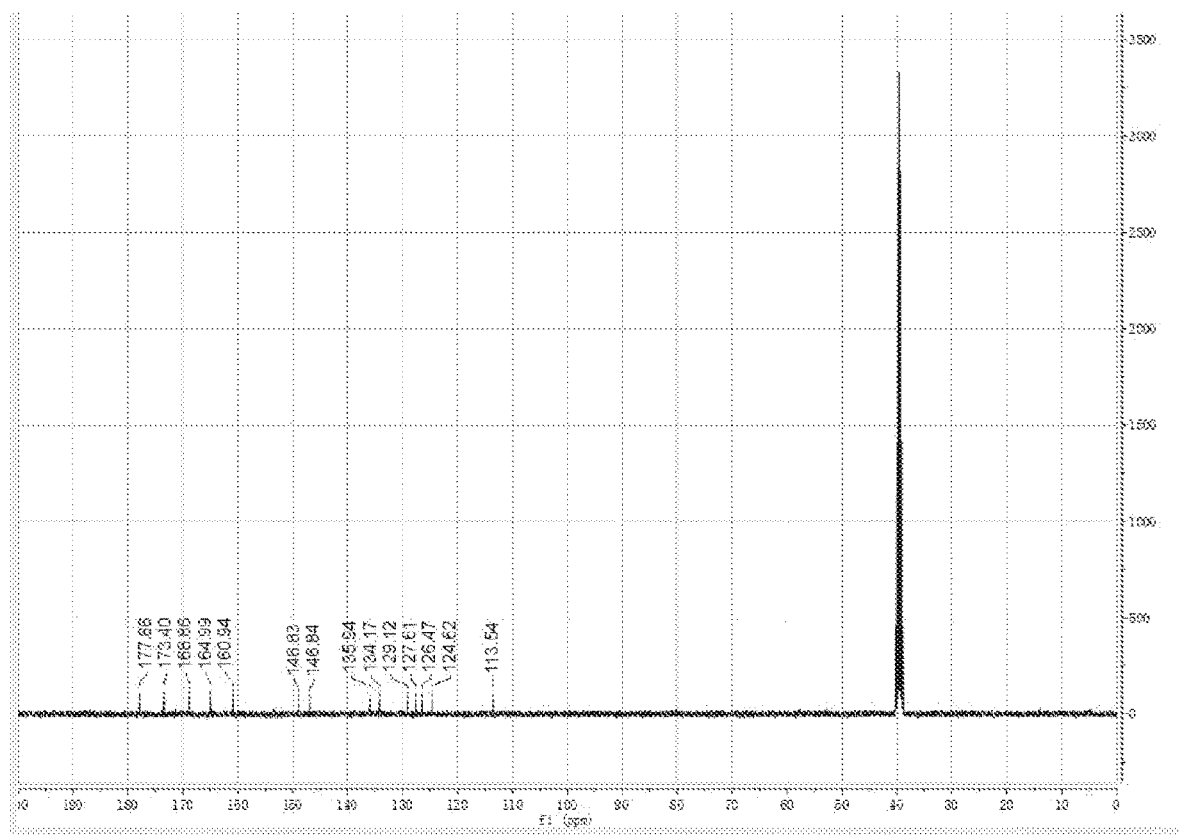
FIG. 23 shows a $^{13}$C-NMR spectrum of PQQ, that is, pyrroloquinoline quinone.

It should be noted that the following detailed description is exemplary and is intended to provide a further description of the present invention. All technical and scientific terms used herein have the same meaning as commonly understood by one of ordinary skill in the art to which this invention belongs, unless otherwise indicated.

However, as described in the background, in the existing route involving the full chemical synthesis of PQQ in the prior art, the key step is that at the later stage of reaction, the methoxy-pyrroloquinoline intermediate needs to be oxidized into a pyrroloquinoline quinone intermediate by ammonium cerium nitrate (CAN). Although the process has a high selectivity to product, the consumption of ammonium cerium nitrate is extremely large (more than 8 times the weight of the raw material), and the optimum yield of this step is only approximately 60% due to the difficulty in the separation and purification. In addition, the high price of cerium ammonium nitrate makes the overall synthesis cost of PQQ high. In order to solve the above technical problems, the present invention proposes an improved route for synthesizing PQQ.

The development of a new PQQ synthesis route, especially to avoid the use of ammonium cerium nitrate, has become a key way to cheap and large-scale synthesis of PQQ. In one embodiment of the present application, a reaction intermediate for synthesizing PQQ is provided, which is a 4,5-disubstituted-1H-pyrrolo(2,3-f)quinolin-2,7,9-tricarboxylate compound, or an analog, isomer or derivative thereof, having a structure of Formula I:

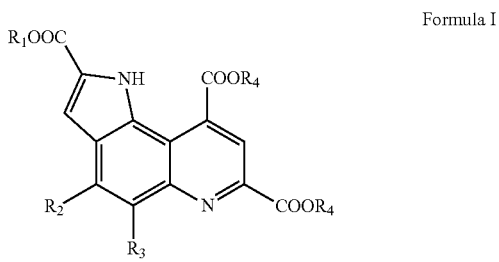

Formula I where $R_1$ and $R_4$ are each independently an atom or group selected from hydrogen, a linear or branched C1-8 alkyl group, a deuterated linear or branched C1-8 alkyl group, an aralkyl group, or a substituted aryl group;

$R_2$ is independently an atom or group selected from halogens, a linear or branched C1-8 alkoxy group, or a deuterated linear or branched C1-8 alkoxy group; and $R_3$ is independently an atom or group selected from a linear or branched C1-8 alkoxy group, or a deuterated linear or branched C1-8 alkoxy group.

In another embodiment of the present application, an intermediate for synthesizing the compound of Formula I is provided, which has a structure of Formula III:

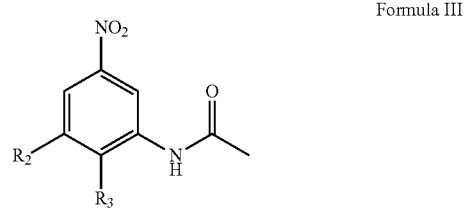

Formula III where $R_2$ is independently an atom or group selected from halogens, a linear or branched C1-8 alkoxy group, or a deuterated linear or branched C1-8 alkyl group; and $R_3$ is independently an atom or group selected from a linear or branched C1-8 alkoxy group, or a deuterated linear or branched C1-8 alkoxy group.

In some specific embodiments of the present invention, when $R_3$=OMe and $R_2$ is respectively Br, Cl, I, or OMe in Formula III, the synthesis route is as follows:

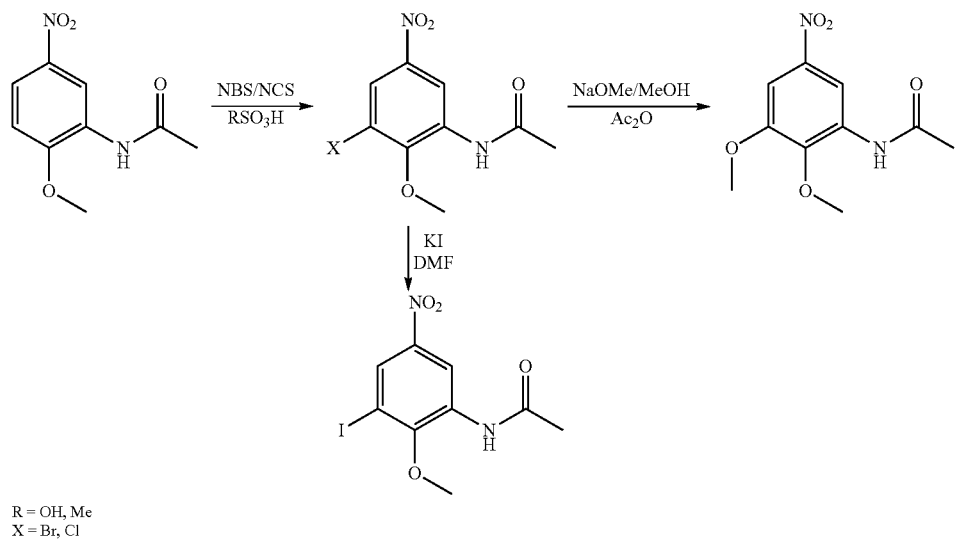

R = OH, Me
X = Br, Cl

In the existing route involving the full chemical synthesis of PQQ, the key step is that at the later stage of reaction, the methoxy-pyrroloquinoline intermediate needs to be mildly oxidized into a pyrroloquinoline quinone intermediate by ammonium cerium nitrate (CAN). The oxidant is expensive and required to be used in a large amount. To improve the synthesis process of PQQ, the present application provides a novel reaction intermediate for synthesizing PQQ, namely the compound of Formula I. By introducing a readily oxidizable and stable substituent on the compound of Formula I, the reaction is allowed to proceed without the need for expensive oxidant in subsequent preparation of PQQ. Therefore, the improvement on the compound of Formula I is mainly attributed to the introduction of the $R_2$ substituent group as compared with the prior art. The key step in the introduction of the $R_2$ substituent group is the synthesis of the compound og Formula III.

In the prior art, the substitution commonly found on the aromatic ring are mainly halogenation, nitrosation, sulfonation reaction, alkylation, acylation, and others. An alkoxy group is attached to a position adjacent to the position where the $R_2$ substituent group is intended to be introduced on the aromatic ring structure of the present application. The applicant found in the experiment that it is difficult to introduce the substituent group to the adjacent position by a conventional substitution reaction due to the presence of the alkoxy group.

Based on this, the applicant has attempted to introduce an $R_2$ substituent group to the compound of Formula III by a relatively easy halogenation reaction. In the prior art, the halogenation on the aromatic ring is generally carried out by the following methods. Description is made by taking bromination as an example.

(1) Bromine is used as a bromine source, Fe or ferric bromide is used as a catalyst, and a halogenated alkane is used as solvent for bromination.

(2) A dilute acid-water solution is used as a solvent and $BrO_3$ is used as a bromine source for bromination.

(3) NBS is used as a bromine source and an organic acid is used as a solvent for bromination.

However, attempts are made to carry out the halogenation reaction on the aromatic ring with $Br_2/Fe/CH_2Cl_2$, $Br_2/FeBr_3/CHCl_3$, $Br_2/FeBr_3/CCl_4$, $Br_2/FeBr_3/HAc$, $Br_2/FeBr_3/$ THF, $NaBrO_3/H_2SO_4$—$H_2O$, $KBrO_3/HAc$—$H_2O$, NBS/HAc, and other systems, that is, to introduce an $R_2$ substituent group to the compound of Formula III, in the earlier studies of the present application. However, the resulting products are heterogeneous, and almost no or only trace amount of the target product is present, and therefore the introduction of an $R_2$ substituent group on the compound of Formula III cannot be achieved.

Therefore, for a particularly specific compound involved in the present application, how to carry out the halogenation reaction on the aromatic ring to introduce an $R_2$ substituent group is a difficulty encountered in the study of the present application, which cannot be solved by the conventional methods in the prior art.

After repeated experiments and exploration, finally in this application, NBS or NCS is used as a halogen source, and concentrated sulfuric acid or methanesulfonic acid is used as a solvent; a substrate is added, and then reacted to obtain the product with high efficiency. In this way, the introduction of an $R_2$ substituent group to the compound of Formula III is achieved. The introduced $R_2$ substituent group may be a halogen, or a linear or branched alkoxy group. These groups are readily oxidizable and relatively stable, and are very favorable for the subsequent oxidation reaction to prepare PQQ; and no expensive oxidant is needed, thereby greatly reducing the preparation cost of PQQ.

In another embodiment of the present application, in order to prepare the compound of Formula I, the present application further provides a method for preparing the compound of Formula I, which comprises specifically:

(1) acetylating Compound a that is a raw material to obtain Compound b;

(2) halogenating/substituting Compound b to obtain Compound c;

(3) subjecting Compound c to nitro reduction to obtain Compound d;

(4) obtaining Compound e by Fischer synthesis by diazotizing Compound d, and then reacting with 2-methyl acetoacetate;

(5) deacylating Compound e to obtain Compound f; and (6) obtaining the compound of Formula I by Skraup reaction by condensing Compound f with 2-oxopentendioate.

The technical synthesis route is as follows.
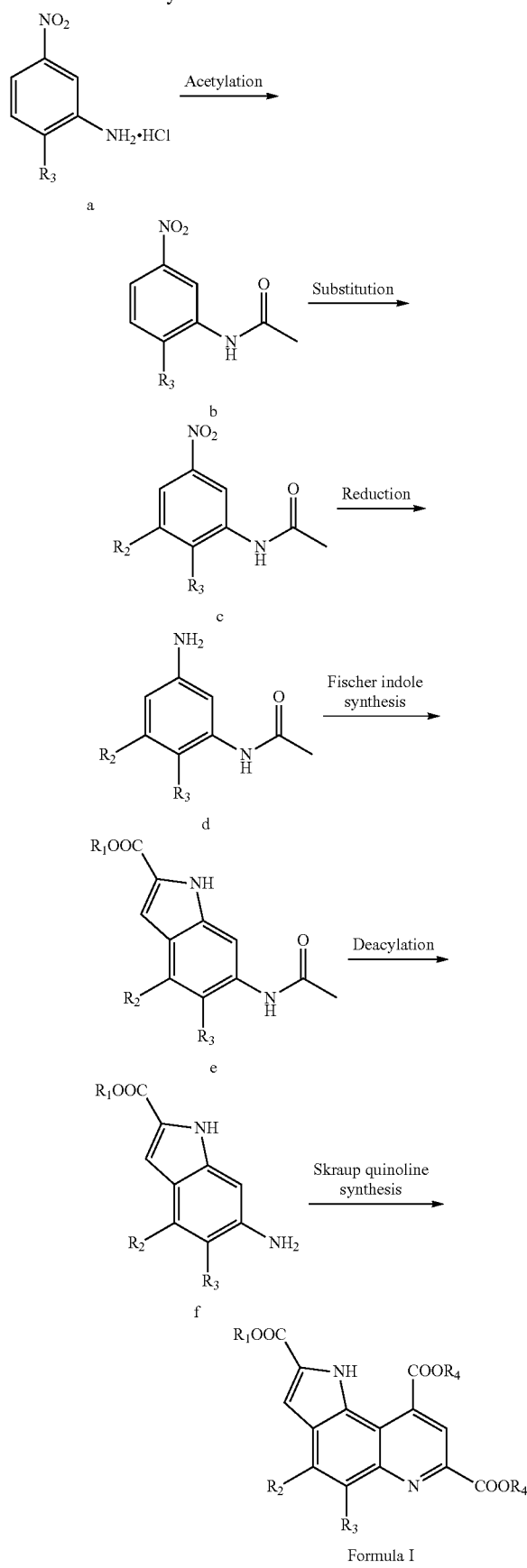
In some specific embodiments of the present invention, in Formula I, when $R_1=R_4=Et$, $R_2=Br$, and $R_3=OMe$, the compound of Formula I is prepared through a synthesis route below:
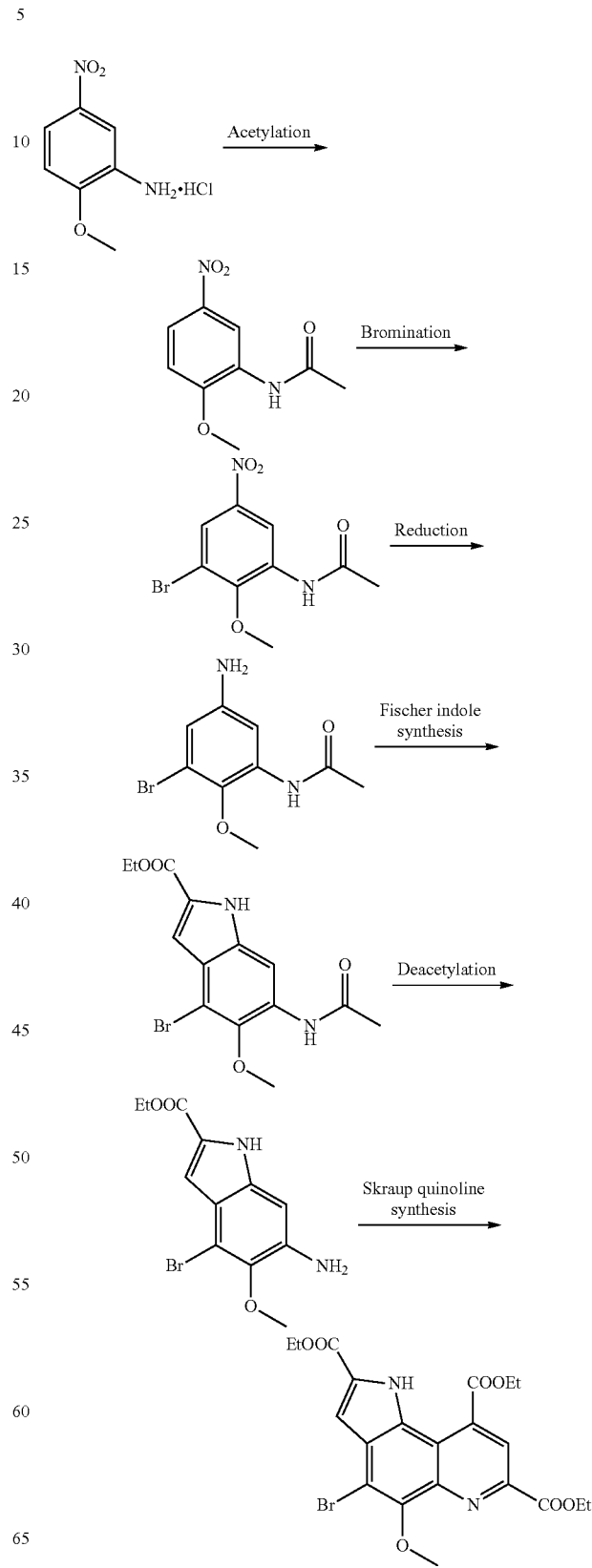

In some other specific embodiments of the present invention, in Formula I, when $R_1=R_4=H$, $R_2=OMe$, and $R_3=OMe$, the compound of Formula I is prepared through a synthesis route below:
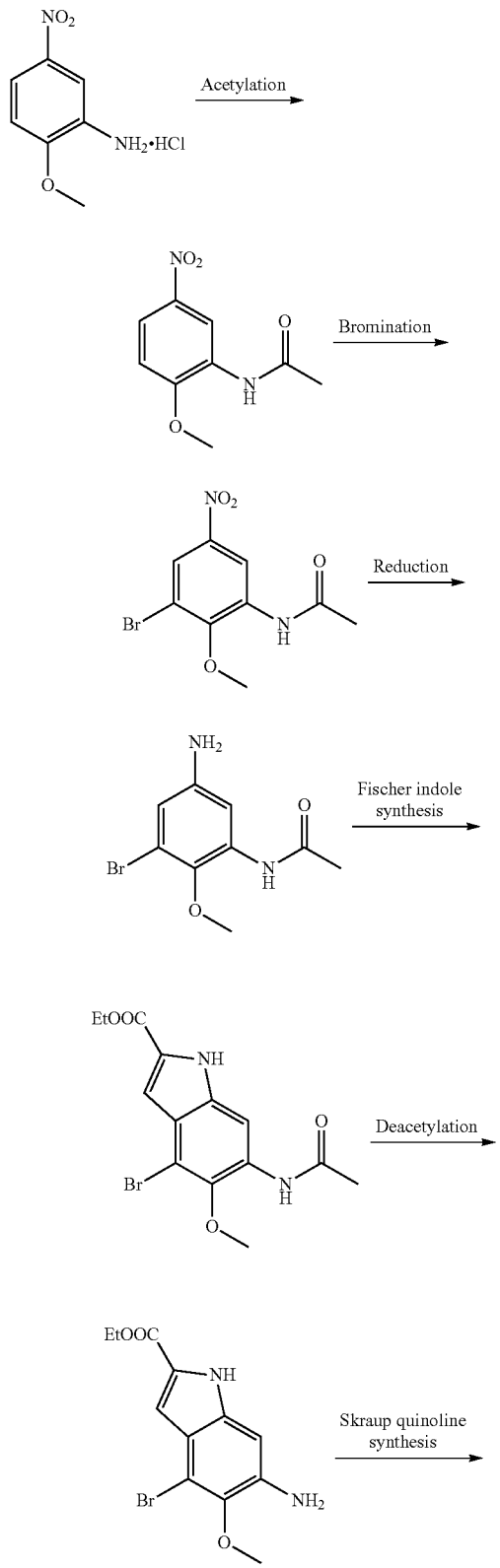
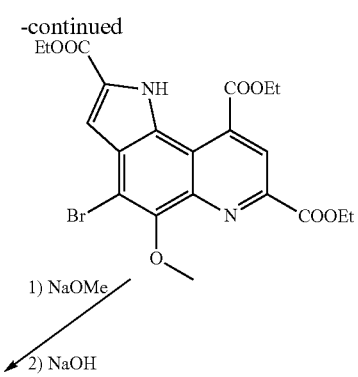
In some other specific embodiments of the present invention, in Formula I, when $R_1=R_4=Et$, $R_2=OEt$, and $R_3=OMe$, the compound of Formula I is prepared through a synthesis route below:
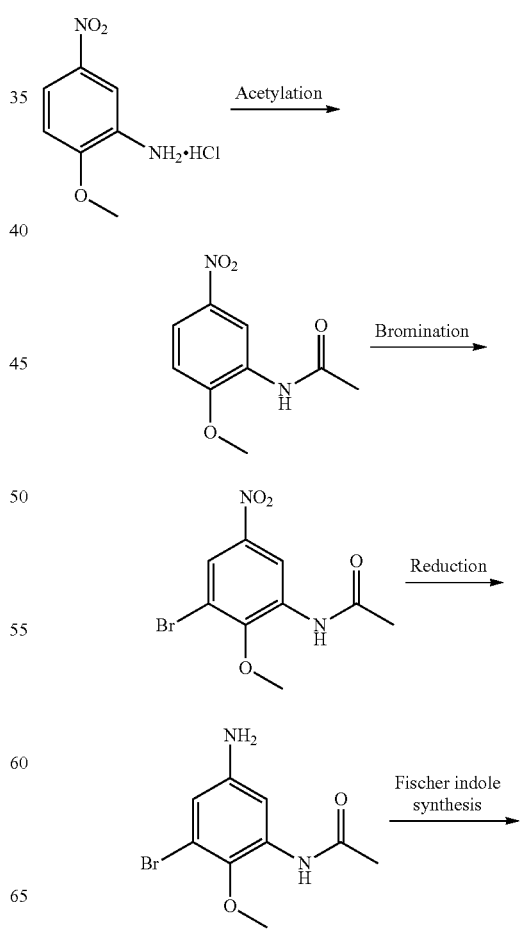

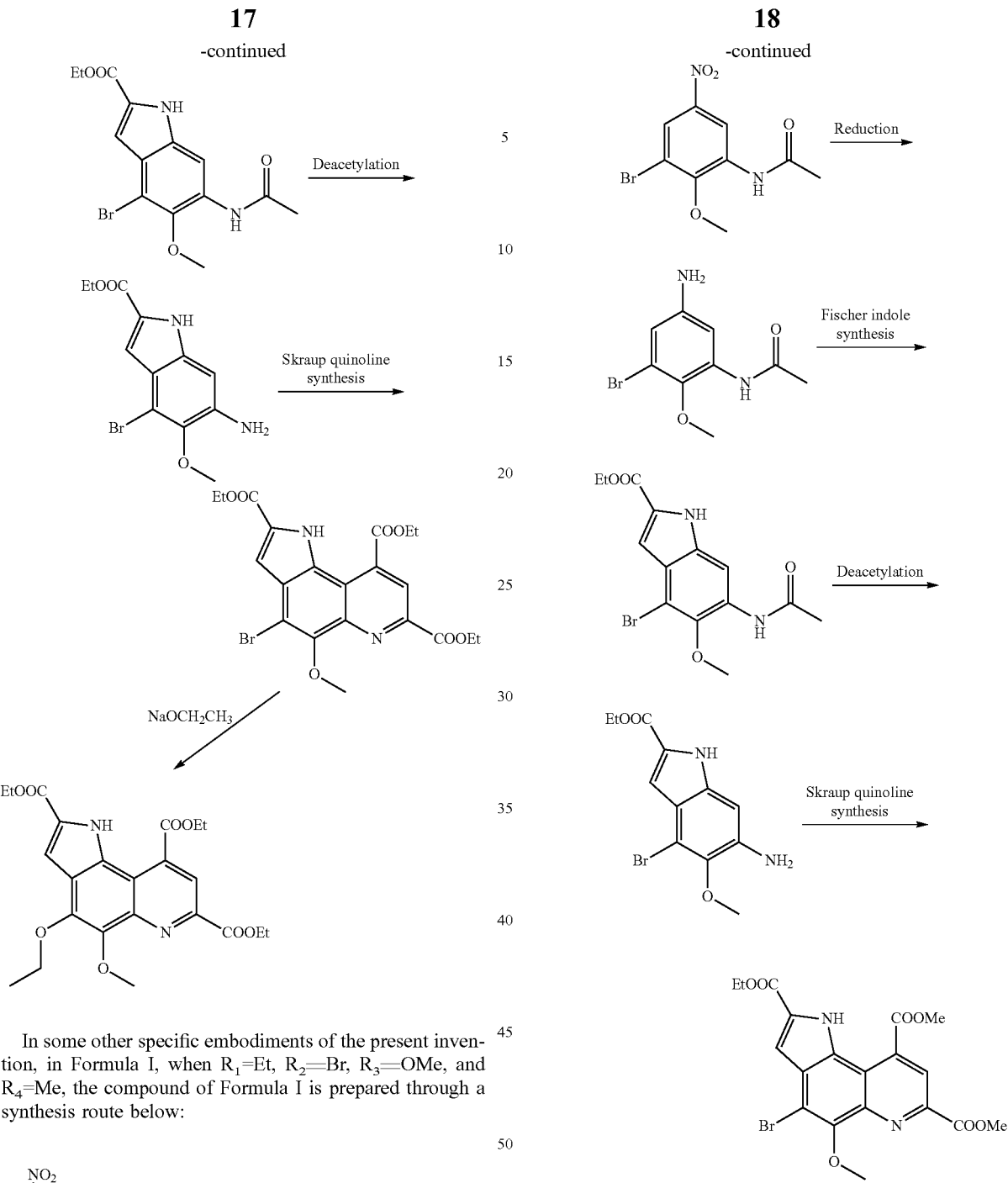

In some other specific embodiments of the present invention, in Formula I, when $R_1$=Et, $R_2$=Br, $R_3$=OMe, and $R_4$=Me, the compound of Formula I is prepared through a synthesis route below:

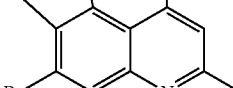

From the description of the above preparation methods and technical routes, those skilled in the art can clearly learn how to carry out the synthesis of the reaction intermediate of Formula I for PQQ without further definition.

In another embodiment of the present application, a method for synthesizing PQQ is provided, which comprises the following steps:

(1) reacting the compound of Formula I with a base or a protonic acid to obtain a compound of formula VI;

(2) reacting the compound of Formula VI with a protonic acid to obtain reduced PQQ, that is, PQP; and (3) oxidizing PQP with an oxidizing agent to obtain PQQ.

The route for synthesizing PQQ of the present invention is:

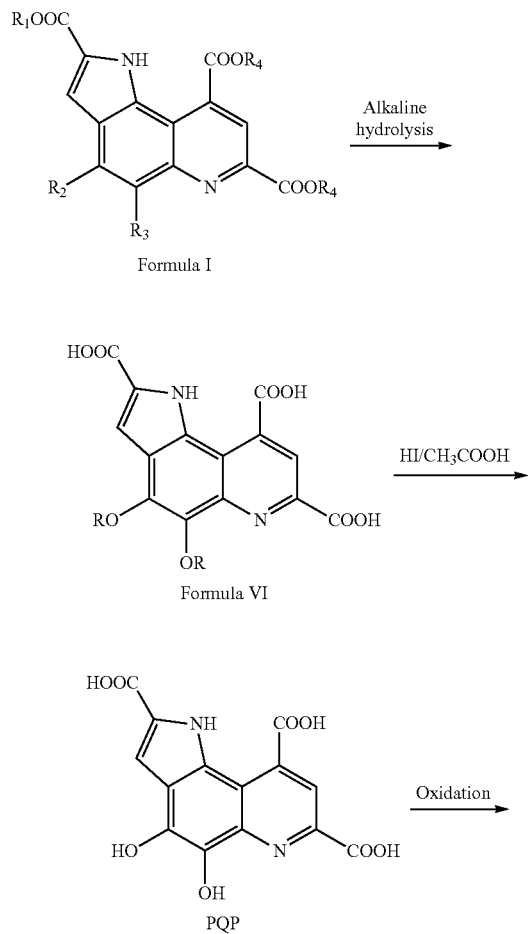

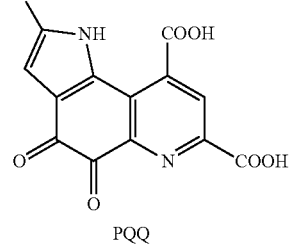

where in Formula VI, R=Me or Et.

In the present invention, the compound of Formula I is used as a reaction intermediate for synthesizing PQQ, and an alkoxy-pyrroloquinoline can be oxidized into pyrroloquinoline quinone under mild temperature conditions (30-40° C.) without further oxidation. The separation and purification are simple, and therefore the product has a high molar yield of 85% or more.

To enable those skilled in the art to more clearly understand the technical solutions of the present invention, the technical solutions of the present invention will be described in detail below in conjunction with specific examples and comparative examples.

EXAMPLE 1

Synthesis of Compound of Formula III

When $R_3$=OMe and $R_2$ is respectively Br, Cl, I, or OMe in Formula III, the route is as follows:

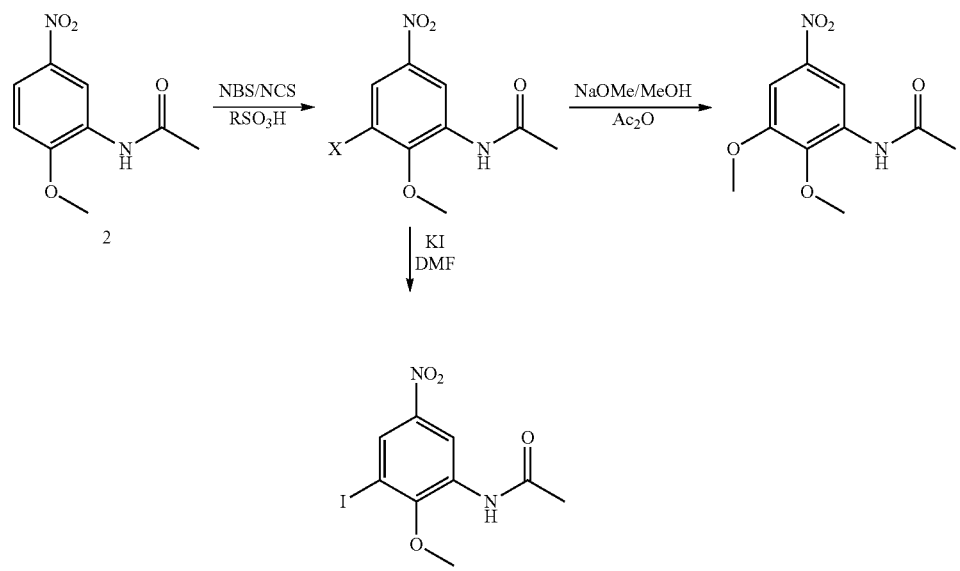

R = OH, Me
X = Br, Cl (1) Synthesis of Compound of Formula III when $R_2$ is Br (namely, 2-methoxy-3-bromo-5-nitro-acetylaniline, Designated as Compound 3):

Synthesis Method I:

100 g of Compound 2 was slowly fed to 500 g of concentrated sulfuric acid while cooled in ice water, stirred to dissolve it, and mixed uniformly. 95 g of NBS was added, and reacted for 12 hrs at 25° C. after complete dissolution. After the reaction was completed, the reaction solution was added to 5000 g of water to precipitate a solid out. The solid was filtered under suction, washed to pH 5-6, filtered under suction, and dried to obtain 128 g of Compound 3. Molar yield: 93%, HPLC purity: 98.5%.

Synthesis Method II:

100 g of Compound 2 was slowly fed to 500 g of methanesulfonic acid while cooled in ice water, stirred to dissolve it, and mixed uniformly. 95 g of NBS was added, and reacted for 12 hrs at 25° C. after complete dissolution. After the reaction was completed, the reaction solution was added to 5000 g of water to precipitate a solid out. The solid was filtered under suction, washed to pH 5-6, filtered under suction, and dried to obtain 130 g of Compound 3. Molar yield: 94.5%, HPLC purity: 98.8%.

ESI (M/Z): 290[M+H];

$^1$H-NMR (400 MHz, DMSO-$D_6$) δ 9.91 (s, 1H), 9.03 (d, J=2.8 Hz, 1H), 8.18 (d, J=2.8 Hz, 1H), 3.85 (s, 3H), 2.20 (s, 3H).

(2) Synthesis of Compound of Formula III when $R_2$ is Cl (namely, 2-methoxy-3-chloro-5-nitro-acetylaniline):

100 g of Compound 2 was slowly fed to 500 g of concentrated sulfuric acid while cooled in ice water, stirred to dissolve it, and mixed uniformly. 75 g of NCS was added, and reacted for 36 hrs at 50° C. after complete dissolution. After the reaction was completed, the reaction solution was added to 5000 g of water to precipitate a solid out. The solid was filtered under suction, washed to pH 5-6, filtered under suction, and dried to obtain 98 g of 2-methoxy-3-chloro-5-nitro-acetylaniline. Ms=244.5, Molar yield: 84.2%, HPLC purity: 98.5%.

ESI (M/Z): 246.5[M+H];

$^1$H-NMR (400 MHz, DMSO-$D_6$) δ 9.90 (s, 1H), 9.02 (d, J=2.8 Hz, 1H), 8.08 (d, J=2.8 Hz, 1H), 3.88 (s, 3H), 2.20 (s, 3H).

(3) Synthesis of Compound of Formula III when $R_2$ is I 100 g of Compound 3 and 500 g of KI were fed to 1500 g of DMF, heated to 120° C. and reacted for 8 hrs. After the reaction was completed, the solvent was evaporated to dryness under reduced pressure. Distilled water was added, and stirred to precipitate a solid out which was then filtered, and dried to give 94 g of 2-methoxy-3-iodo-5-nitro-acetylaniline. Molar yield: 81%, HPLC purity: 97.6%. ESI (M/Z): 337[M+H].

(4) Synthesis of Compound of Formula III when $R_2$ is OMe 374 g of 30% sodium methoxide/methanol solution was fed to a reaction flask, and evaporated under reduced pressure to remove 85% of methanol. 600 g of dioxane, 100 g of Compound 3, and 10 g of CuI were added to the residue, heated to 90° C. and reacted under reflux for 12 hrs. After the reaction was completed, the solvent was recovered under reduced pressure, and 600 g of water was added to the residue, and stirred to precipitate a solid out. The obtained solid was fed to 353 g of acetic anhydride, heated to 80° C. and reacted with stirring for 4 hrs. After the completion of the reaction, the solvent was recovered under reduced pressure, and the residue was washed with 600 g of distilled water. A crystal was precipitated, recrystallized in anhydrous ethanol, and dried to give 68 g of 2-methoxy-3-methoxy-5-nitro-acetylaniline. Ms=240, Molar yield: 82%, HPLC purity: 97.8%. ESI (M/Z): 241[M+H].

EXAMPLE 2

Preparation of Compound 7 (where in Formula I, $R_1$=$R_4$=Et, $R_2$=Br, and $R_3$=OMe) (namely, diethyl 4-bromo-5-methoxy-1H-pyrrolo(2,3-f)quinolin-2,7,9-tricarboxylate)

The synthesis route is as follows.

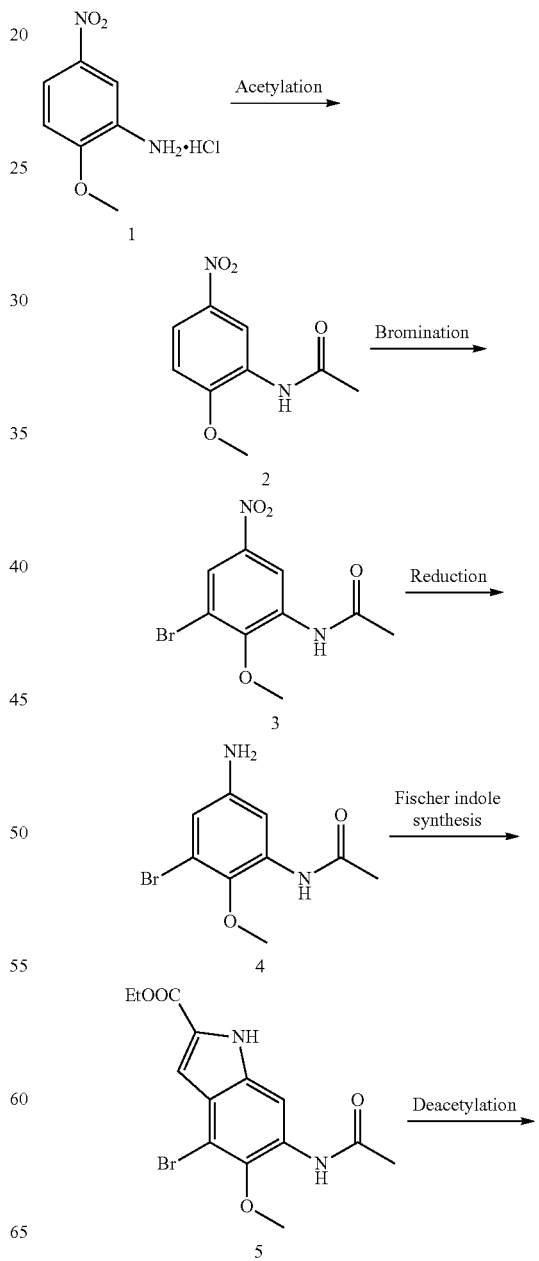

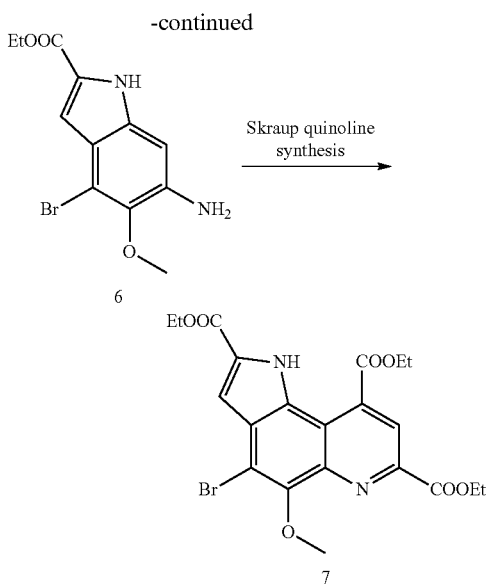

The specific preparation method is as follows.

(1) Preparation of Compound 2

100 g of Compound 1, that is, 2-methoxy-5-nitroaniline hydrochloride, was added to 1500 g of water, stirred to dissolve it, and then filtered after the solid was almost completely dissolved. 40% NaOH solution was added to the filtrate to adjust the solution to pH>4. The solution was extracted three times with 200 g of ethyl acetate. The organic phases were combined, washed with 500 g of saturated brine, and then dried over 100 g of anhydrous magnesium sulfate. After filtration, the solvent was rotary evaporated to dryness under reduced pressure at 50° C. to give an orange-red solid. The orange-red solid was dissolved in 600 g of acetic anhydride, heated to 80° C. and reacted for 4 hrs. After the reaction was completed, most of the solvent was removed by evaporation under reduced pressure. After cooling, the residue was added to 1000 g of ice water to precipitate a large amount of a solid. The solid was filtered out, repeatedly washed with water until it was not significantly acidic, and dried to obtain 81 g of Compound 2. Molar yield: 78.88%, HPLC purity: 98.2%.

ESI (M/Z): 211[M+H].

(2) Preparation of Compound 3

100 g of Compound 2 was slowly fed to 500 g of concentrated sulfuric acid while cooled in ice water, stirred to dissolve it, and mixed uniformly. 95 g of NBS was added, and reacted for 12 hrs at 25° C. after complete dissolution. After the reaction was completed, the reaction solution was added to 5000 g of water to precipitate a solid out. The solid was filtered under suction, washed to pH 5-6, filtered under suction, and dried to obtain 128 g of Compound 3. Molar yield: 93%, HPLC purity: 98.5%.
ESI (M/Z): 290[M+H];

$^1$H-NMR (400 MHz, DMSO-D$_6$) δ 9.91 (s, 1H), 9.03 (d, J=2.8 Hz, 1H), 8.18 (d, J=2.8 Hz, 1H), 3.85 (s, 3H), 2.20 (s, 3H).

(3) Preparation of Compound 4

100 g of iron powder was added to 1000 g of a 10% acetic acid solution, heated to 80° C. and reacted with stirring for 1 hr. After the reaction solution was slightly cold, 150 g of Compound 3 was slowly added. After the mixture was uniformly mixed, the mixture was heated to 75-80° C. and reacted with stirring for 6 hrs, until the reaction was completed. The reaction solution was cooled to room temperature, adjusted to pH 8-9 with a saturated sodium carbonate solution and filtered under suction. After the solid was repeatedly washed with hot ethanol, the ethanol solution was collected, and ethanol was rotary evaporated to dryness under reduced pressure to precipitate a large amount of crystal which was then filtered out under suction.

The solid was collected and dried to obtain 110.5 g of white granular crystal, that is, Compound 4. Molar yield: 82.2%, HPLC purity: 98.9%.

ESI (M/Z): 260[M+H].

(4) Preparation of Compound 5

100 g of 32-37% concentrated hydrochloric acid was fed to a reaction flask, and 50 g of Compound 4 was slowly added at −25° C., uniformly mixed and then stirred for 60 min. 45 g of 40% sodium nitrite solution was slowly added dropwise to a reaction flask while the temperature was controlled to not greater than −10° C., and stirred for 15 min. 45 g of 40% HBF$_4$ solution was added dropwise while the temperature was controlled to not greater than 0° C. After the addition was completed, the temperature was raised to 5° C. A cream yellow turbid solution was obtained, which was filtered under suction. The filter cake was rinsed with cold alcohol, and the solid was collected.

The solid obtained in the previous step was dissolved in 200 g of ethanol, and 32 g of ethyl 2-methylacetoacetate was slowly added while the temperature was controlled to lower than 0° C. After the addition, a NaOH solution was added dropwise, while the temperature was controlled to not greater than 0° C. After the addition was completed, the mixture was stirred at room temperature for 12 hrs. After the reaction was completed, the reaction solution was filtered under suction. The solid was washed with water, filtered under suction and dried. 100 g of a light orange-red solid was obtained.

The orange-red solid obtained in the previous step was dissolved in 500 g of sulfuric acid and stirred at room temperature for 24 hrs. After completion of the reaction, the reaction solution was added to 2000 g of ice water to precipitate a pale yellow solid, which was filtered under suction, washed twice with water, and dried. The solid was recrystallized twice in ethanol, to obtain 45 g of Compound 5. Molar yield: 65.66%, HPLC purity: 99%.

ESI (M/Z): 356[M+H].

(5) Preparation of Compound 6

100 g of Compound 5 was added to a mixed solution of 500 g of ethanol and 100 g of concentrated hydrochloric acid, stirred until uniform, heated to reflux, and reacted for 8 hrs. The ethanol was evaporated off under reduced pressure. After cooling to room temperature, the residue was added to 1000 g of ice water to precipitate a large amount of a light brown solid, which was then filtered under suction. The solid was washed twice with water and dried.

The light brown solid obtained in the previous step was added to 1000 g of a 15% NaOH solution, and stirred at room temperature for 24 hrs. The solid was filtered under suction, washed with water until it was not significantly basic, and then dried, to obtain 56 g of a brown solid, that is, Compound 6. Molar yield: 63.5%, HPLC purity: 98.7%.

ESI(M/Z): 314[M+H];

$^1$H-NMR (400 MHz, DMSO-D$_6$) δ 11.53 (d, J=1.5 Hz, 1H), 6.82 (dd, J=2.2, 0.6 Hz, 1H), 6.66 (d, J=0.7 Hz, 1H), 5.34 (s, 2H), 4.28 (q, J=7.1 Hz, 2H), 3.70 (s, 3H), 1.31 (t, J=7.1 Hz, 3H).

(6) Preparation of Compound 7

100 g of Compound 6 was dissolved in 500 g of dichloromethane, and 1000 g of diethyl 2-oxopentendioate was added thereto, and stirred at room temperature for 24 hrs. The solvent was evaporated to dryness under reduced pressure to obtain a dark brown viscous material. The viscous material was dissolved in hot ethanol, and filtered while hot. The filtrate was placed in a refrigerator overnight to precipitate a pale yellow solid. The solid was filtered under suction and dried to obtain 93 g of Compound 7. Molar yield:

58.93%, HPLC purity: 99.2%.

ESI(M/Z): 495[M+H];

$^1$H-NMR (400 MHz, DMSO-D$_6$) δ 12.33 (d, J=1.9 Hz, 1H), 8.64 (s, 1H), 7.18 (d, J=2.3 Hz, 1H), 4.57 (q, J=7.1 Hz, 2H), 4.47 (q, J=7.1 Hz, 2H), 4.40 (q, J=7.1 Hz, 2H), 4.08 (s, 3H), 1.46 (t, J=7.1 Hz, 3H), 1.42 (t, J=7.1 Hz, 3H), 1.38 (t, J=7.1 Hz, 3H).

EXAMPLE 3

Preparation of Compound 7

Compound 2 was Prepared Through a Method that Followed.

100 g of Compound 1, i.e., 2-methoxy-5-nitroaniline hydrochloride, was dissolved in 600 g of acetic anhydride, and heated to 80° C. for 8 hrs, and the tail gas was absorbed with a NaOH solution. After the reaction was completed, most of the solvent was removed by evaporation under reduced pressure. After cooling, the residue was added to 1000 g of ice water to precipitate a large amount of a solid. The solid was filtered out, repeatedly washed with water until it was not significantly acidic, and dried to obtain 96 g of Compound 2. Molar yield: 93.48%, HPLC purity: 98.7%.

ESI (M/Z): 211[M+H].

The remaining steps were the same as those in Example 1.

EXAMPLE 4

Preparation of Compound 7

Compound 3 was Prepared Through a Method that Followed.

100 g of Compound 2 was slowly fed to 500 g of methanesulfonic acid while cooled in ice water, stirred to dissolve it, and mixed uniformly. 95 g of NBS was added, and reacted for 12 hrs at 25° C. after complete dissolution. After the reaction was completed, the reaction solution was added to 5000 g of water to precipitate a solid out. The solid was filtered under suction, washed to pH 5-6, filtered under suction, and dried to obtain 130 g of Compound 3. Molar yield: 94.5%, HPLC purity: 98.8%.

The remaining steps were the same as those in Example 1.

EXAMPLE 5

Preparation of Compound 8 (where in Formula I, R$_1$=R$_4$=H, and R$_2$=R$_3$=OMe), namely, 4,5-dimethoxy-1H-pyrrolo(2,3-f)quinolin-2,7,9-tricarboxylic acid The specific preparation method is as follows.

Compound 7 was prepared, as described in Example 2, 3 or 4.

100 g of the solid Compound 7 and 20 g of CuI were added to 800 g of dioxane, and stirred until uniform. 500 g of a 30% sodium methoxide/methanol solution was slowly added. After mixing well, the resulting system was heated and reacted under reflux for 8 hrs. After completion of the reaction, the mixture was cooled slightly, and the solvent was recovered under reduced pressure at a temperature of 80° C. at most. After recovery, the mixture was cooled to 30° C., and 1000 g of a 10% NaOH solution was slowly added thereto, and heated to reflux for 6 hrs. After the reaction was completed, it was cooled to room temperature and filtered under suction. Ice was added to the filtrate, and then concentrated hydrochloric acid was slowly added to adjust the pH to less than 2. The resulting solution was filtered under suction, and the solid was washed with distilled water until it was not significantly acidic, and then dried to obtain 65 g of Compound 8 as a dark orange bulk solid. Molar yield: 89.2%, HPLC purity: 98.3%.

ESI (M/Z): 359[M−H];

$^1$H-NMR (400 MHz, DMSO-D$_6$) δ 13.49 (d, J=5.7 Hz, 1H), 12.56 (s, 1H), 8.62 (d, J=38.1 Hz, 1H), 7.32 (s, 1H), 4.23 (s, 3H), 4.03 (m, 3H).

The synthesis route is as follows.

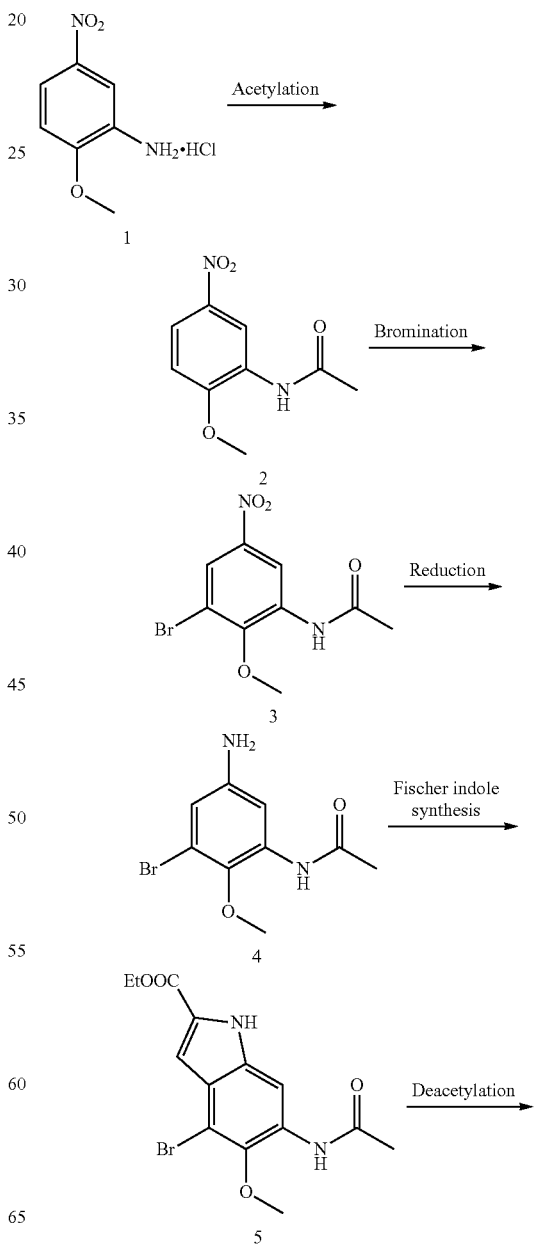

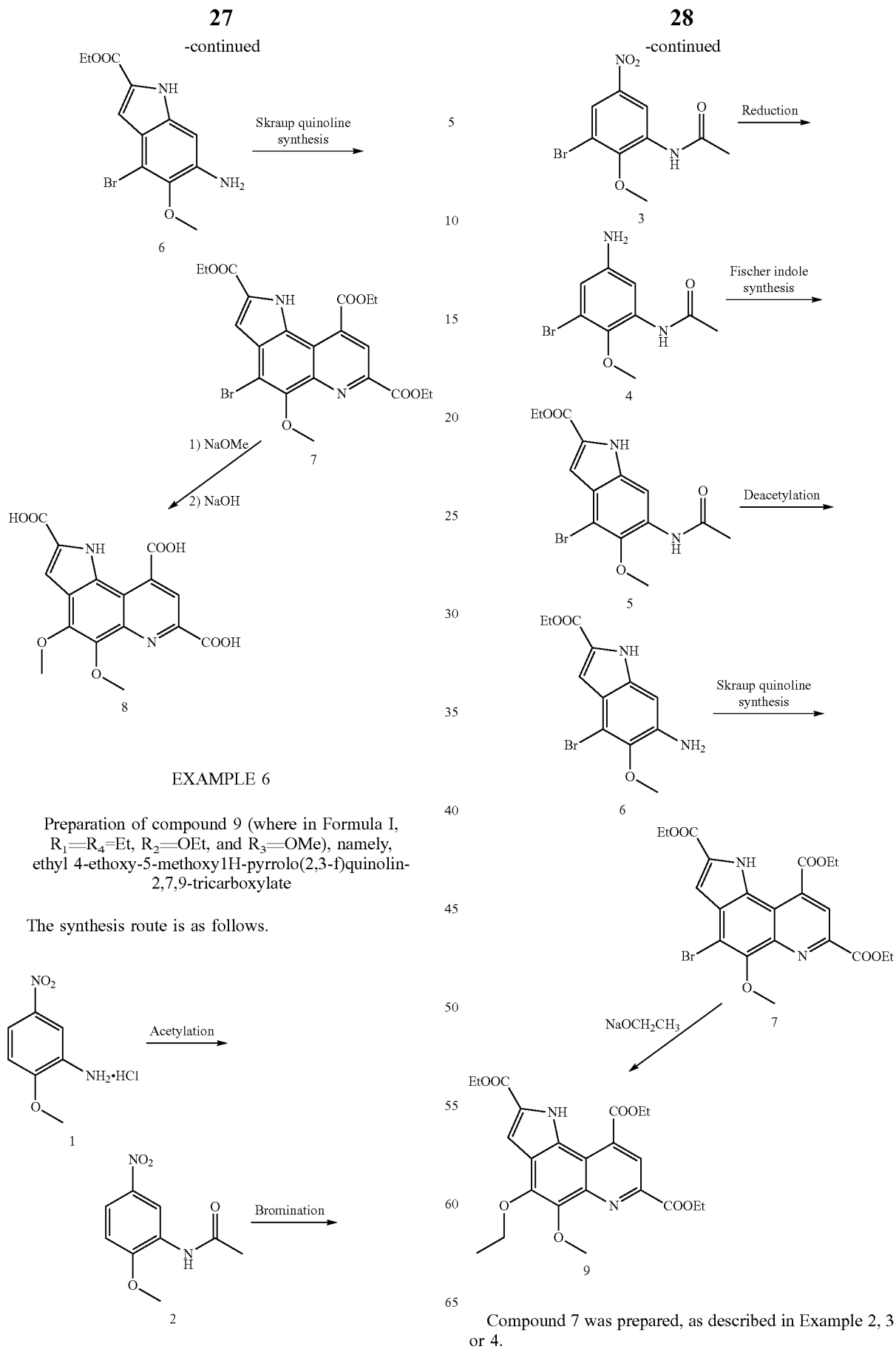
EXAMPLE 6
Preparation of compound 9 (where in Formula I, $R_1$=$R_4$=Et, $R_2$=OEt, and $R_3$=OMe), namely, ethyl 4-ethoxy-5-methoxy1H-pyrrolo(2,3-f)quinolin-2,7,9-tricarboxylate
The synthesis route is as follows.
Compound 7 was prepared, as described in Example 2, 3 or 4.

100 g of Compound 7 and 20 g of CuI were added to 800 g of dioxane, and stirred until uniform. 500 g of a 30% sodium ethoxide solution was slowly added. After mixing well, the resulting system was heated and reacted under reflux for 8 hrs. After the reaction was completed, the reaction solution was slightly cooled, and the solvent was recovered under reduced pressure at a temperature of 80° C. at most. After recovery, the residue was cooled to 30° C. or less, distilled water was added, and the pH was adjusted to 2 to 3 with dilute hydrochloric acid.

A solid material was precipitated out, filtered under suction, and washed with water. The solid material was collected and dried to give 80 g of Compound 9. Molar yield: 86.1%, HPLC purity: 99.1%. ESI (M/Z): 460[M+H].

EXAMPLE 7

Preparation of Compound 11 (where in Formula I, $R_1$=Et, $R_2$=Br, $R_3$=OMe, and $R_4$=Me), namely 2-ethyl 7,9-dimethyl 4-bromo-5-methoxy-1H-pyrrolo(2,3-f)quinolin-2,7,9-tricarboxylate The synthesis route is as follows.

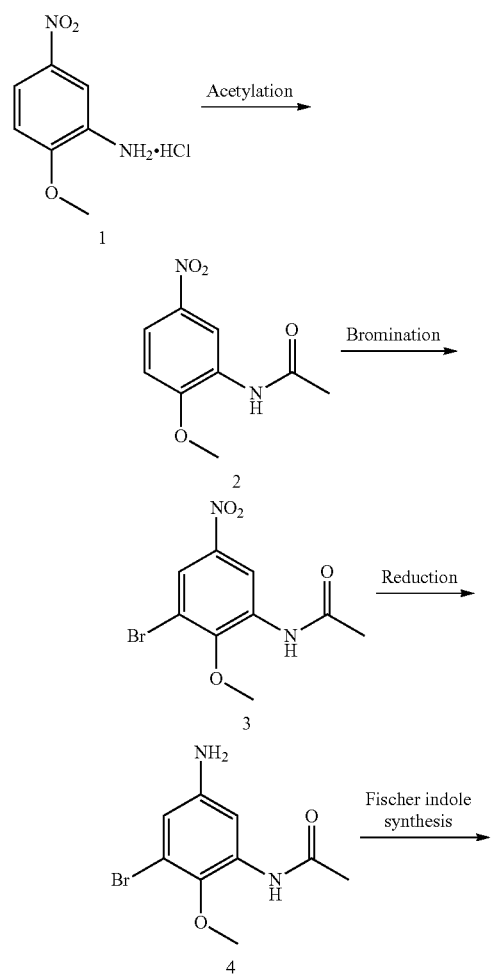

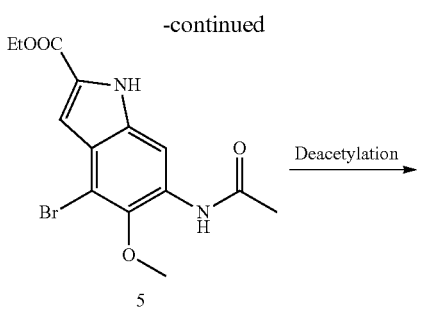

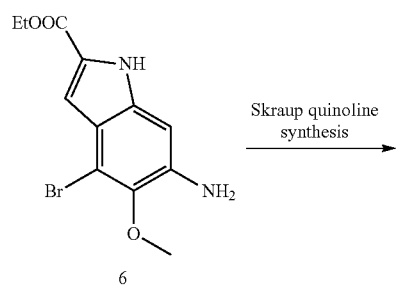

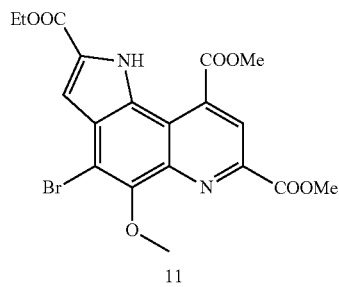

100 g of Compound 6 was dissolved in 500 g of dichloromethane, and 1000 g of dimethyl 2-oxopentendioate was added thereto, and stirred at room temperature for 24 hrs. The solvent was evaporated to dryness under reduced pressure to obtain a dark brown viscous material. The viscous material was dissolved in hot ethanol, and filtered while hot.

The filtrate was placed in a refrigerator overnight to precipitate a pale yellow solid. The solid was filtered under suction and dried to obtain 87 g of Compound 11. Molar yield: 58.4%, HPLC purity: 98.6%.

ESI (M/Z):467[M+H].

1H-NMR (400 MHz, DMSO-D6) δ 12.46 (d, J=1.9 Hz, 1H), 8.73 (s, 1H), 7.28 (d, J=2.3 Hz, 1H), 4.42 (q, J=7.1 Hz, 2H), 4.08 (s, 3H), 4.02 (s, 6H), 1.39 (t, J=7.1 Hz, 3H).

EXAMPLE 8

Preparation of PQQ

Compound 8 prepared in Example 5 was used as a reaction intermediate for the synthesis of PQQ, and the synthesis route was as follows.

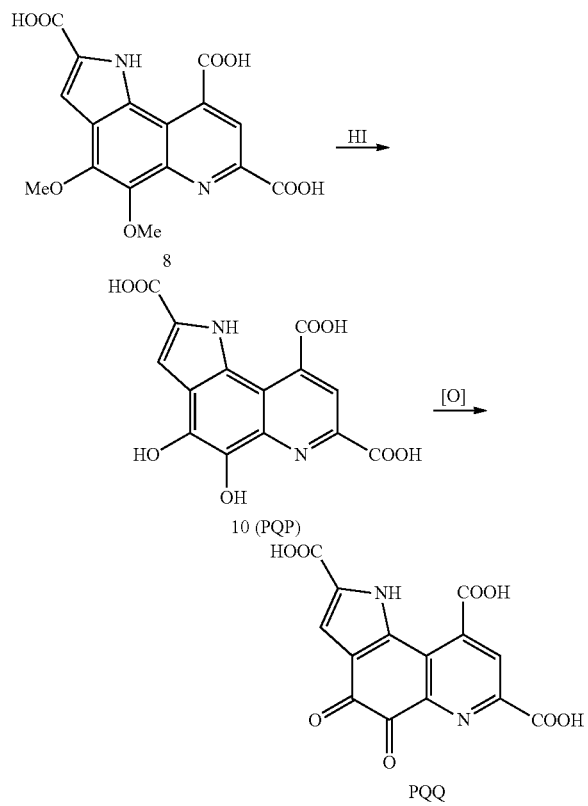

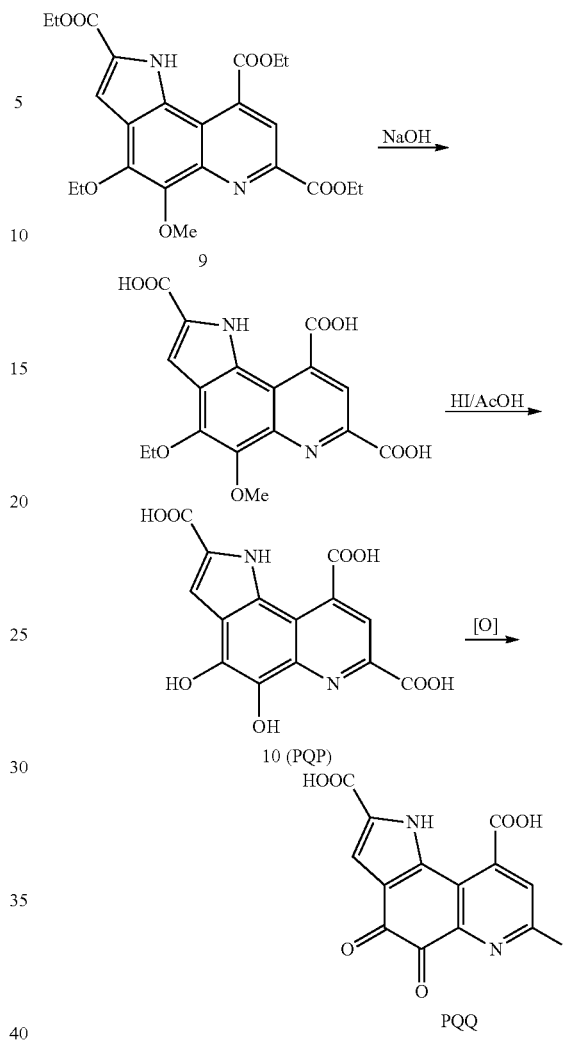

The synthesis method was specifically as follows.

(1) Preparation of Compound 10 (PQP): 100 g of the solid Compound 8 was added to 500 g of acetic acid, and 300 g of a 40% HI solution was added dropwise, uniformly mixed, and refluxed for 8 hrs. After the reaction was completed, the reaction solution was added to 2500 g of ice water to precipitate a solid, which was filtered under suction, washed until it was not significantly acidic, and dried. The solid was recrystallized in ethanol to give 73 g of Compound 10 (PQP). Molar yield: 85.5%, HPLC purity: 98.4%. ESI (M/Z): 331[M−H].

(2) Preparation of pyrroloquinoline quinone (PQQ) 100 g of the solid Compound 10 (PQP), was added to 500 g of a 30% hydrogen peroxide solution, maintained at a temperature of 35° C., and stirred for 24 hrs. After cooling, the reaction solution was filtered, and the solid was dried and dissolved in 500 g of concentrated sulfuric acid. Then the sulfuric acid solution was added to 2500 g of ice water to precipitate a large amount of a red solid. The solid was filtered out, repeatedly washed with water until it was not significantly acidic, and dried to obtain 86 g of PQQ as a red powdered solid. Molar yield: 86.5%, HPLC purity: 99.6%. ESI (M/Z):329[M−H].

EXAMPLE 9

Preparation of PQQ

Compound 9 prepared in Example 6 was used as a reaction intermediate for the synthesis of PQQ, and the synthesis route was as follows.

The synthesis method was specifically as follows.

(1) Preparation of Compound 10: 100 g of Compound 9 was added to 1000 g of a 10% NaOH solution, and heated to reflux for 6 hrs. After the reaction was completed, it was cooled to room temperature and filtered under suction. Ice was added to the filtrate, and then concentrated hydrochloric acid was slowly added to adjust the pH to less than 2. The resulting solution was filtered under suction, and the solid was washed with distilled water until it was not significantly acidic, and then dried. The resulting solid was added to 500 g of acetic acid, and 300 g of a 40% HI solution was added dropwise, mixed uniformly and refluxed for 8 hrs. After the reaction was completed, the reaction solution was added to 2500 g of ice water to precipitate a solid, which was filtered under suction, washed until it was not significantly acidic, and dried. The solid was recrystallized in ethanol to give 65 g of Compound 10 (PQP). Molar yield: 89.86%, HPLC purity: 98.1%. ESI (M/Z): 331[M−H].

(2) Preparation of pyrroloquinoline quinone (PQQ) 100 g of the solid Compound 10 (PQP), was added to 500 g of a 30% hydrogen peroxide solution, maintained at a temperature of 35° C., and stirred for 24 hrs. After cooling, the reaction solution was filtered, and the solid was dried and dissolved in 500 g of concentrated sulfuric acid. Then the sulfuric acid solution was added to 2500 g of ice water to precipitate a large amount of a red solid. The solid was filtered out, repeatedly washed with water until it was not significantly acidic, and dried to obtain 85 g of PQQ as a red powdered solid. Molar yield: 85.6%, HPLC purity: 99.6%.

ESI (M/Z):329[M−H];

$^1$H-NMR (400 MHz, DMSO-D$_6$) δ 13.23 (s, 1H), 8.60 (s, 1H), 7.21 (d, J=2.2 Hz, 1H).

The above examples are preferred embodiments of the present invention, but the embodiments of the present invention are not limited to thereto. Any other changes, modifications, replacements, combinations, and simplifications may be made without departing from the spirit and scope of the present invention, which are all embraced in the scope of the present invention.

What is claimed is:

1. A compound according to Formula I,

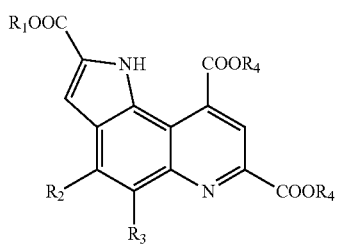

Formula I where R$_1$ and R$_4$ are each independently an atom or group selected from hydrogen, a linear or branched C1-8 alkyl group, a deuterated linear or branched C1-8 alkyl group, or an aralkyl group;

R$_2$ is independently an atom or group selected from halogens; and

R$_3$ is independently an atom or group selected from a linear or branched C1-8 alkoxy group, or a deuterated linear or branched C1-8 alkoxy group.

2. The compound according to claim 1, wherein R$_1$ and R$_4$ are each independently selected from hydrogen, methyl or ethyl; R$_2$ is selected from halogens; and R$_3$ is selected from a C1-4 alkoxy group.

3. The compound according to claim 1, which is selected from

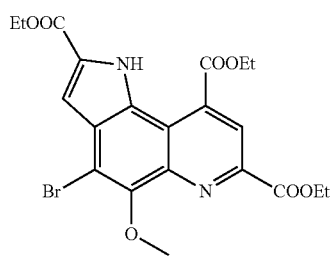 [SMILES: CCOC(=O)c1cc(C(=O)OCC)c2c(n1)c(OC)c(OCC)c1cc(C(=O)OCC)[nH]c12]

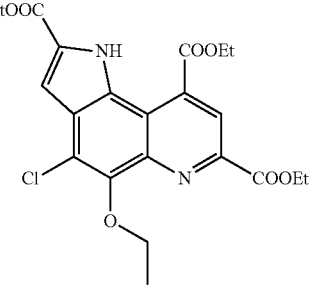

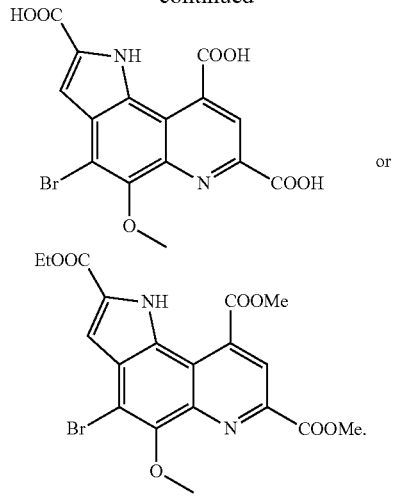

4. A method for preparing the compound of Formula I,

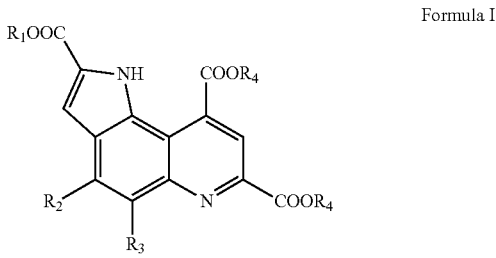

Formula I comprising a step of obtaining a compound of Formula IV by a nitro reducing reaction of a compound of Formula III, and then obtaining a compound of Formula II by Fischer indole synthesis and deacylation using the compound of Formula IV; and a step of obtaining the compound of Formula I by subjecting the compound of Formula II to Skraup quinoline synthesis,

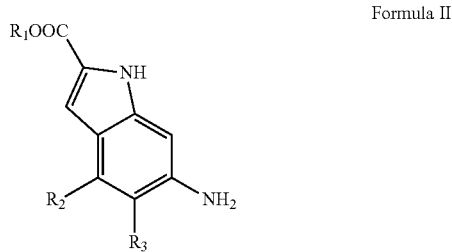

Formula II where in Formula II, R$_1$ is independently an atom or group selected from hydrogen, a linear or branched C1-8 alkyl group, a deuterated linear or branched C1-8 alkyl group, or an aralkyl group;

R$_2$ is independently an atom or group selected from halogens; and

R$_3$ is independently an atom or group selected from linear or branched C1-8 alkoxy group, deuterated linear or branched C1-8 alkoxy group;

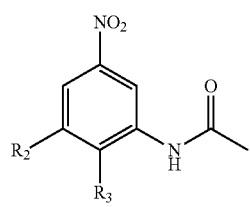

Formula III where in Formula III,
R₂ is independently an atom or group selected from halogens; and
R₃ is independently an atom or group selected from a linear or branched C1-8 alkoxy group, or a deuterated linear or branched C1-8 alkoxy group;

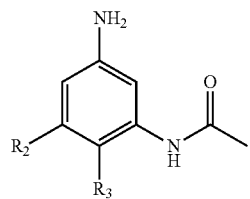

Formula IV where in Formula IV,
R₂ is independently an atom or group selected from halogens; and
R₃ is independently an atom or group selected from a linear or branched C1-8 alkoxy group, or a deuterated linear or branched C1-8 alkoxy group.

5. The method according to claim 4, wherein R₂ in Formula III is chlorine or bromine.

6. The method according to claim 4, wherein R₂ in Formula III is bromine.

7. The method according to claim 4, wherein a method for obtaining the compound of Formula I by subjecting the compound of Formula II to Skraup quinoline synthesis comprises specifically dissolving the compound of Formula II in an organic solvent, adding dimethyl 2-oxopentendioate or diethyl 2-oxopentendioate, reacting with stirring at room temperature, evaporating off the solvent, and recrystallizing the residue.

8. A method for synthesizing pyrroloquinoline quinone (PQQ), comprising the steps of:
(1) reacting a compound of the Formula I according to claim 1 with a sodium methoxide/sodium ethoxide to obtain a compound of formula VI;
(2) reacting the compound of Formula VI with a protonic acid to obtain reduced pyrroloquinoline quinone (PQP); and
(3) oxidizing PQP with an oxidizing agent to obtain PQQ;
the structure of formula VI is:

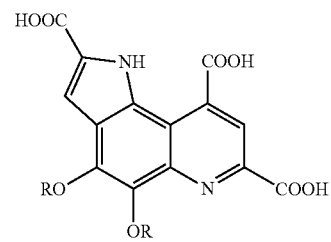

wherein R=Me or Et.

9. The synthesis method according to claim 8, comprising a method for preparing the compound of Formula I,

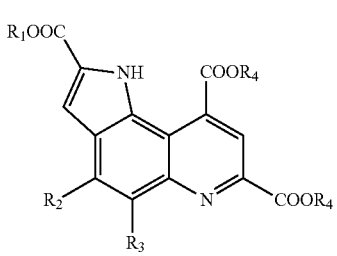

Formula I comprising a step of obtaining a compound of Formula IV by a nitro reducing reaction of a compound of Formula III, and then obtaining a compound of Formula II by Fischer indole synthesis and deacylation using the compound of Formula IV; and a step of obtaining the compound of Formula I by subjecting the compound of Formula II to Skraup quinoline synthesis,

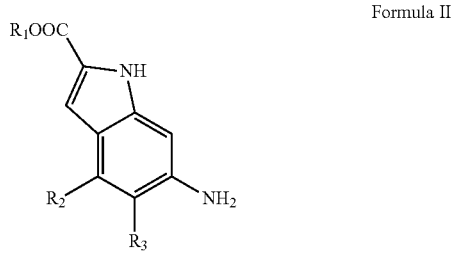

Formula II where in Formula II, R₁ is independently an atom or group selected from hydrogen, a linear or branched C1-8 alkyl group, a deuterated linear or branched C1-8 alkyl group, an aralkyl group;

R₂ is independently an atom or group selected from halogens; and

R₃ is independently an atom or group selected from linear or branched C1-8 alkoxy group, deuterated linear or branched C1-8 alkoxy group;

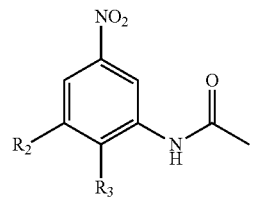

Formula III where in Formula III,
R₂ is independently an atom or group selected from halogens; and
R₃ is independently an atom or group selected from a linear or branched C1-8 alkoxy group, or a deuterated linear or branched C1-8 alkoxy group;

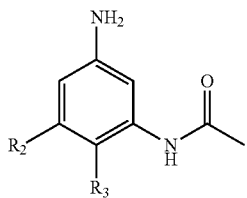

Formula IV where in Formula IV,

R$_2$ is independently an atom or group selected from halogens; and

R$_3$ is independently an atom or group selected from a linear or branched C1-8 alkoxy group, or a deuterated linear or branched C1-8 alkoxy group.

10. The synthesis method according to claim 8, wherein N-bromosuccinimide (NBS) or N-chlorosuccinimide (NCS) is used as a halogen source, concentrated sulfuric acid or methanesulfonic acid is used as a solvent, a substrate is added, and then reacted, to obtain the compound of Formula III, wherein the substrate has a structural formula of:

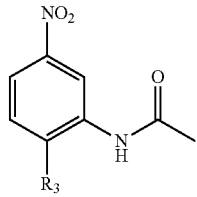

wherein R$_3$ is independently an atom or group selected from a linear or branched C1-8 alkoxy group, or a deuterated linear or branched C1-8 alkoxy group.

11. The synthesis method according to claim 9, wherein the halogen source is NBS.

12. The synthesis method according to claim 9, wherein the molar ratio of the substrate, halogen source, and solvent is 1:(0.95-1.5):(3-12).

13. The synthesis method according to claim 9, wherein the reaction temperature for obtaining the compound of Formula III is 20-60° C.

14. The synthesis method according to claim 8, wherein in Step (2), the method for reacting the compound of Formula VI with a protonic acid to obtain reduced pyrroloquinoline quinone (PQP), comprises: adding the compound of Formula VI to acetic acid, adding a protonic acid solution dropwise, mixing uniformly, reacting under reflux, adding the reaction solution to ice water after the reaction is completed to precipitate a solid out, filtering under suction, washing, drying, and recrystallizing in ethanol.

15. The synthesis method according to claim 8, wherein in Step (2), the protonic acid is hydroiodic acid, hydrochloric acid or hydrobromic acid.

16. The synthesis method according to claim 15, wherein the protonic acid is hydroiodic acid.

17. The synthesis method according to claim 8, wherein in Step (3), the oxidizing agent is hydrogen peroxide, concentrated sulfuric acid, concentrated nitric acid or ozone.

* * * * *